US010550288B2

(12) United States Patent
Hoshino et al.

(10) Patent No.: US 10,550,288 B2
(45) Date of Patent: Feb. 4, 2020

(54) FLUORINATED ETHER COMPOUND, FLUORINATED ETHER COMPOSITION, COATING LIQUID AND ARTICLE

(71) Applicant: AGC Inc., Chiyoda-ku (JP)

(72) Inventors: Taiki Hoshino, Chiyoda-ku (JP); Kiyotaka Takao, Chiyoda-ku (JP); Kazue Toda, Chiyoda-ku (JP); Kenji Ishizeki, Chiyoda-ku (JP); Akira Isobe, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 68 days.

(21) Appl. No.: 15/877,489

(22) Filed: Jan. 23, 2018

(65) Prior Publication Data

US 2018/0148606 A1 May 31, 2018

Related U.S. Application Data

(63) Continuation of application No. PCT/JP2016/075354, filed on Aug. 30, 2016.

(30) Foreign Application Priority Data

Sep. 1, 2015 (JP) ................................. 2015-171986

(51) Int. Cl.
| | |
|---|---|
| *C09D 201/04* | (2006.01) |
| *B32B 33/00* | (2006.01) |
| *C08F 259/08* | (2006.01) |
| *C09D 201/10* | (2006.01) |
| *C07F 7/10* | (2006.01) |
| *C07F 7/12* | (2006.01) |

(52) U.S. Cl.
CPC ............ *C09D 201/04* (2013.01); *B32B 33/00* (2013.01); *C08F 259/08* (2013.01); *C09D 201/10* (2013.01); *B32B 2307/7265* (2013.01); *B32B 2307/746* (2013.01)

(58) Field of Classification Search
USPC ...................... 556/420, 431, 435; 528/36, 31
See application file for complete search history.

(56) References Cited

U.S. PATENT DOCUMENTS

| | | | | |
|---|---|---|---|---|
| 2011/0124532 A1* | 5/2011 | Maurer | ................. | C07F 7/1804 507/205 |
| 2016/0040039 A1 | 2/2016 | Yamane et al. | | |
| 2016/0304665 A1* | 10/2016 | Sakoh | ................. | C08G 65/007 |
| 2019/0002635 A1 | 1/2019 | Mitsuhashi et al. | | |

FOREIGN PATENT DOCUMENTS

| | | |
|---|---|---|
| EP | 3 085 749 A1 | 10/2016 |
| JP | 01-211593 | 8/1989 |
| JP | 2014-070163 | 4/2014 |
| JP | 2014-144935 | 8/2014 |
| JP | 2015-168785 | 9/2015 |
| JP | 2016-037541 A | 3/2016 |
| WO | 2009/008380 | 1/2009 |
| WO | 2013/121984 | 8/2013 |
| WO | WO 2017/022437 A1 | 2/2017 |

OTHER PUBLICATIONS

International Search Report dated Nov. 8, 2016 in PCT/JP2016/075354 filed Aug. 30, 2016.
Mangzhu Zhao, et al., "Oxidation of Primary Alcohols to Carboxylic Acids with Sodium Chlorite Catalyzed by TEMPO and Bleach," J. Org. Chem. 1999, vol. 64, pp. 2564-2566.

* cited by examiner

*Primary Examiner* — Fred M Teskin
(74) *Attorney, Agent, or Firm* — Oblon, McClelland, Maier & Neustadt, L.L.P.

(57) ABSTRACT

To provide a fluorinated ether compound, a fluorinated ether composition and a coating liquid that are able to form a surface layer which is excellent in water/oil repellency, abrasion resistance, fingerprint stain removability, lubricity and outer appearance, and an article having such a surface layer. A fluorinated ether compound represented by $A^1\text{-O-}(R^{f1}O)_{m1}\text{-}Q^1\text{-}[C(O)N(R^1)]_{p1}\text{-}R^{11}\text{-}C[\text{-}R^{12}\text{-}SiR^{13}{}_{n1}X^1{}_{3\text{-}n1}]_3$, wherein $A^1$ is a $C_{1\text{-}20}$ perfluoroalkyl group; $R^{f1}$ is a fluoroalkylene group having no branched structure; m1 is an integer from 2 to 210; $Q^1$ is a single bond or a fluoroalkylene group having no branched structure; $R^1$ is a hydrogen atom, etc.; p1 is 0 or 1; $R^{11}$ is a single bond, an alkylene group, etc.; $R^{12}$ is an alkylene group, etc.; $R^{13}$ is a monovalent hydrocarbon group, etc.; $X^1$ is a hydrolyzable group; and n1 is an integer of from 0 to 2.

16 Claims, No Drawings

FLUORINATED ETHER COMPOUND, FLUORINATED ETHER COMPOSITION, COATING LIQUID AND ARTICLE

TECHNICAL FIELD

The present invention relates to a fluorinated ether compound, a fluorinated ether composition, a coating liquid and an article.

BACKGROUND ART

A fluorinated compound exhibits high lubricity, water/oil repellency, etc. and thus is suitably used for a surface treatment agent. When water/oil repellency is imparted to the surface of a substrate by such a surface treatment agent, it will be easy to wipe off stain from the surface of the substrate, whereby removability of stain will be improved. Among such fluorinated compounds, a fluorinated ether compound having a poly(oxyperfluoroalkylene) chain with an ether bond (—O—) present at middle in a perfluoroalkyl chain, is particularly excellent in removability of stain of e.g. oils or fats.

A surface treatment agent containing the fluorinated ether compound is used in an application where it is desired to maintain, for a long period of time, a performance (abrasion resistance) whereby water/oil repellency is less likely to be lowered even if rubbed repeatedly with a finger, and a performance (fingerprint stain removability) whereby a fingerprint adhered to a surface can be readily removed by wiping, for example, as a surface treatment agent for a member constituting the surface to be touched with a finger, of a touch panel.

In order to impart abrasion resistance to the surface layer formed on the surface of a substrate, for example, a hydrolyzable silyl group may be introduced at a terminal of the fluorinated ether compound, so that the fluorinated ether compound and the substrate will be chemically bonded. As a fluorinated ether compound for the purpose of forming a surface layer excellent in abrasion resistance, a fluorinated ether compound has been proposed wherein to each of both terminals of the fluorinated ether compound, three hydrolyzable silyl groups are introduced via a branched structure by pentaerythritol (Patent Document 1).

PRIOR ART DOCUMENT

Patent Document

Patent Document 1: JP-A-2014-070163

DISCLOSURE OF INVENTION

Technical Problem

According to the findings by the present inventors, the fluorinated ether compound described in Patent Document 1 has the following problems.

Both terminals of the fluorinated ether compound are immobilized, as hydrolyzable silyl groups at both terminals are reacted with the substrate, or by an intermolecular reaction. Therefore, lubricity (smoothness when the surface layer is touched with a finger) and abrasion resistance of the surface layer become insufficient.

The poly(oxyperfluoroalkylene) chain has a branched structure, whereby fingerprint stain removal properties and lubricity of the surface layer become insufficient.

Since the content of non-fluorinated portions (a branched structure by pentaerythritol and three hydrolyzable silyl groups) at terminals, is large, the outer appearance of the surface layer tends to be deteriorated. The reason is considered to be such that among molecules of the fluorinated ether compound, hydrolyzable silyl groups are likely to be agglomerated one another, and in the coating liquid, or during drying after the coating liquid is applied to the surface of a substrate, hydrolyzable silyl groups will be agglomerated and reacted one another to form a non-uniform layer.

An object of the present invention is to provide a fluorinated ether compound, a fluorinated ether composition and a coating liquid, capable of forming a surface layer excellent in water/oil repellency, abrasion resistance, fingerprint stain removability, lubricity and outer appearance, and an article having a surface layer excellent in water/oil repellency, abrasion resistance, fingerprint stain removability, lubricity and outer appearance.

Solution to Problem

The present invention provides a fluorinated ether compound, a fluorinated ether composition, a coating liquid and an article having the following constructions [1] to [14].

[1] A fluorinated ether compound represented by the following formula (1):

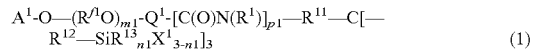

(1)

wherein $A^1$ is a $C_{1-20}$ perfluoroalkyl group, $R^{f1}$ is a fluoroalkylene group having no branched structure, m1 is an integer of from 2 to 210, $(R^{f1}O)_{m1}$ may be one composed of at least two types of $R^{f1}O$, $Q^1$ is a single bond or a fluoroalkylene group having no branched structure, $R^1$ is a hydrogen atom or an alkyl group, p1 is 0 or 1, $R^{11}$ is a single bond, an alkylene group, an alkylene group having an etheric oxygen atom at its terminal (which is the terminal on the side bonded to $C[—R^{12}—SiR^{13}{}_{n1}X^1{}_{3-n1}]_3$), an alkylene group with at least two carbon atoms, having an etheric oxygen atom between its carbon-carbon atoms, or an alkylene group with at least two carbon atoms, having an etheric oxygen atom between its carbon-carbon atoms and at its terminal (which is the terminal on the side bonded to $C[—R^{12}—SiR^{13}{}_{n1}X^1{}_{3-n1}]_3$), $R^{12}$ is an alkylene group, an alkylene group having an etheric oxygen atom at its terminal (but excluding the terminal on the side bonded to Si), or an alkylene group with at least two carbon atoms, having an etheric oxygen atom between its carbon-carbon atoms, $R^{13}$ is a hydrogen atom or a monovalent hydrocarbon group, $X^1$ is a hydrolyzable group, n1 is an integer of from 0 to 2, and three $[—R^{12}—SiR^{13}{}_{n1}X^1{}_{3-n1}]$ may not be all the same group.

[2] The fluorinated ether compound according to [1], wherein the fluorinated ether compound represented by the formula (1) is a fluorinated ether compound represented by the following formula (1-1):

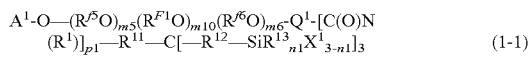

$$A^1\text{-}O\text{—}(R^{f5}O)_{m5}(R^{F1}O)_{m10}(R^{f6}O)_{m6}\text{-}Q^1\text{-}[C(O)N(R^1)]_{p1}\text{—}R^{11}\text{—}C[\text{—}R^{12}\text{—}SiR^{13}{}_{n1}X^1{}_{3-n1}]_3 \quad (1\text{-}1)$$

wherein $A^1$, $Q^1$, $R^1$, $p1$, $R^{11}$, $R^{12}$, $R^{13}$, $X^1$ and $n1$ are the same as in the formula (1), $R^{F1}$ is a perfluoroalkylene group having no branched structure, m10 is an integer of at least 2, and $(R^{F1}O)_{m10}$ may be one composed of at least two types of $R^{F1}O$, $R^{f5}$ is a fluoroalkylene group containing at least one hydrogen atom and having no branched structure, m5 is an integer of from 0 to 4, and when m5 is an integer of from 2 to 4, $(R^{f5}O)_{m5}$ may be one composed of at least two types of $R^{f5}O$, $R^{f6}$ is a fluoroalkylene group containing at least one hydrogen atom and having no branched structure, m6 is an integer of from 0 to 4, and when m6 is an integer of from 2 to 4, $(R^{f6}O)_{m6}$ may be one composed of at least two types of $R^{f6}O$, and m10+m5+m6=m1.

[3] The fluorinated ether compound according to [2], wherein $R^{F1}$ is a $C_{1-6}$ perfluoroalkylene group, and $R^{f5}$ and $R^{f6}$ are each independently a $C_{2-6}$ fluoroalkylene group.

[4] The fluorinated ether compound according to [2] or [3], wherein $R^{f5}$ and $R^{f6}$ are each independently a fluoroalkylene group having one or two hydrogen atoms.

[5] The fluorinated ether compound according to any one of [2] to [4], wherein when p1 is 0, m6 is 1 or 2 and $Q^1$ is a single bond, and $(R^{f6}O)$ bonded to $R^{11}$ is a group represented by $(R^{f7}CH_2O)$, and when p1 is 1, m6 is 0 and $Q^1$ is a fluoroalkylene group.

[6] The fluorinated ether compound according to any one of [2] to [5], wherein m10 is at least 5.

[7] The fluorinated ether compound according to any one of [1] to [6], wherein when $Q^1$ is a fluoroalkylene group, such a fluoroalkylene group is a $C_{1-6}$ perfluoroalkylene group.

[8] The fluorinated ether compound according to any one of [1] to [7], wherein when p1 is 0, $R^{11}$ is a $C_{1-4}$ alkylene group, and when p1 is 1, $R^{11}$ is a single bond or a $C_{1-4}$ alkylene group.

[9] The fluorinated ether compound according to any one of [1] to [8], wherein $R^{12}$ is a $C_{2-6}$ alkylene group, or a $C_{3-8}$ alkylene group having an etheric oxygen atom between carbon atoms.

[10] The fluorinated ether compound according to any one of [1] to [9], which has a number average molecular weight of from 500 to 20,000.

[11] A fluorinated ether composition comprising the fluorinated ether compound as defined any one of [1] to [10], and a fluorinated ether compound other than the fluorinated ether compound represented by the formula (1), characterized in that the total proportion of the fluorinated ether compound represented by the formula (1) and other fluorinated ether compound in the fluorinated ether composition is from 80 to 100 mass %, and the proportion of said other fluorinated ether compound to the total of the fluorinated ether compound represented by the formula (1) and other fluorinated ether compound is more than 0 mass % and less than 40 mass %.

[12] The fluorinated ether composition according to [11], wherein said other fluorinated ether compound is at least one member selected from the group consisting of the following fluorinated ether compound (2), the following fluorinated ether compound (3) and the following fluorinated ether compound (4):

Fluorinated ether compound (2): A fluorinated ether compound wherein in the fluorinated ether compound represented by the formula (1), a group having said $\text{—}C[\text{—}R^{12}\text{—}SiR^{13}{}_{n1}X^1{}_{3-n1}]_3$ is bonded to both sides of said $(R^{f1}O)_{m1}$, Fluorinated ether compound (3): A fluorinated ether compound wherein in the fluorinated ether compound represented by the formula (1), a group having said $A^1$ is bonded to both sides of said $(R^{f1}O)_{m1}$, Fluorinated ether compound (4): A fluorinated ether compound wherein in the fluorinated ether compound represented by the formula (1), said $\text{—}C[R^{12}\text{—}SiR^{13}{}_{n1}X^1{}_{3-n1}]_3$ is substituted by $\text{—}C[\text{—}R^{12}\text{—}SiR^{13}{}_{n1}X^1{}_{3-n1}]_{3-t}[\text{—}R^{15}]_t$ (wherein $R^{15}$ is an unsaturated bond-containing group which becomes $\text{—}R^{12}\text{—}SiR^{13}{}_{n1}X^1{}_{3-n1}$ by addition of $HSiR^{13}{}_{n1}X^1{}_{3-n1}$, or an isomer group of the unsaturated bond-containing group, and t is an integer of 1 to 3.).

[13] A coating liquid characterized by comprising a fluorinated ether compound as defined in any one of [1] to [10] or a fluorinated ether composition as defined in [11] or [12], and a liquid medium.

[14] An article characterized by having a surface layer which is formed of a fluorinated ether compound as defined in any one of [1] to [10] or a fluorinated ether composition as defined in [11] or [12].

Advantageous Effects of Invention

According to the fluorinated ether compound, the fluorinated ether composition and the coating liquid of the present invention, it is possible to form a surface layer excellent in water/oil repellency, abrasion resistance, fingerprint stain removability, lubricity and outer appearance.

The article of the present invention has a surface layer excellent in water/oil repellency, abrasion resistance, fingerprint stain removability, lubricity and outer appearance.

DESCRIPTION OF EMBODIMENTS

In this specification, a compound represented by the formula (1) will be referred to as a compound (1). Compounds represented by other formulae will be referred to in the same manner.

Meanings of the following terms in this specification are as follows.

A "perfluoroalkyl group" means a group having all of hydrogen atoms in an alkyl group substituted by fluorine atoms.

A "fluoroalkylene group" means a group having at least one of hydrogen atoms in an alkylene group substituted by a fluorine atom.

A "perfluoroalkylene group" means a group having all of hydrogen atoms in an alkylene group substituted by fluorine atoms.

The chemical formula of an oxyperfluoroalkylene group shall be written by placing its oxygen atom on the right hand side of the perfluoroalkylene group.

An "etheric oxygen atom" means an oxygen atom to form an ether bond (—O—) between carbon-carbon atoms.

A "hydrolyzable silyl group" means a group capable of forming a silanol group (Si—OH) by hydrolysis. For example, it is $SiR^{13}{}_{n1}X^1{}_{3-n1}$ in the formula (1).

A "surface layer" means a layer formed at the surface of a substrate.

The "number average molecular weight" of a fluorinated ether compound is calculated by the following method by using a NMR analysis.

It is calculated by obtaining the number (average value) of oxyperfluoroalkylene groups based on terminal groups, by $^1$H-NMR and $^{19}$F-NMR. The terminal groups may, for example, be $A^1$ or $SiR^{13}{}_{n1}X^1{}_{3-n1}$ in the formula (1).

[Fluorinated Ether Compound]

The fluorinated ether compound of the present invention (hereinafter referred to also as the present compound) is the compound (1).

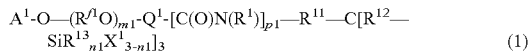

$$A^1\text{-O}-(R^{f1}O)_{m1}\text{-}Q^1\text{-}[C(O)N(R^1)]_{p1}-R^{11}-C[R^{12}-SiR^{13}{}_{n1}X^1{}_{3-n1}]_3 \quad (1)$$

wherein $A^1$ is a $C_{1-20}$ perfluoroalkyl group; $R^{f1}$ is a fluoroalkylene group having no branched structure; m1 is an integer of from 2 to 210; $(R^{f1}O)_{m1}$ may be one composed of at least two types of $R^{f1}O$; $Q^1$ is a single bond or a fluoroalkylene group having no branched structure; $R^1$ is a hydrogen atom or an alkyl group; p1 is 0 or 1; $R^{11}$ is a single bond, an alkylene group, an alkylene group having an etheric oxygen atom at its terminal (which is the terminal on the side bonded to $C[-R^{12}-SiR^{13}{}_{n1}X^1{}_{3-n1}]_3$), an alkylene group with at least two carbon atoms, having an etheric oxygen atom between its carbon-carbon atoms, or an alkylene group with at least two carbon atoms, having an etheric oxygen atom between its carbon-carbon atoms and at its terminal (which is the terminal on the side bonded to $C[-R^{12}-SiR^{13}{}_{n1}X^1{}_{3-n1}]_3$); $R^{12}$ is an alkylene group, an alkylene group having an etheric oxygen atom at its terminal (but excluding the terminal on the side bonded to Si), or an alkylene group with at least two carbon atoms, having an etheric oxygen atom between its carbon-carbon atoms; $R^{13}$ is a hydrogen atom or a monovalent hydrocarbon group; $X^1$ is a hydrolyzable group; n1 is an integer of from 0 to 2; and three $[-R^{12}-SiR^{13}{}_{n1}X^1{}_{3-n1}]$ may not be all the same group.

($A^1$ group)

As $A^1$, from the viewpoint of further excellency in lubricity and abrasion resistance of the surface layer, a $C_{1-10}$ perfluoroalkyl group is preferred, a $C_{1-6}$ perfluoroalkyl group is more preferred, and a $C_{1-3}$ perfluoroalkyl group is particularly preferred.

$A^1$ has $CF_3-$ at its terminal, whereby one terminal of the compound (1) becomes $CF_3-$ and the other terminal becomes a hydrolyzable silyl group. According to the compound (1) having such a structure, a surface layer with a low surface energy can be formed, and such a surface layer is excellent in lubricity and abrasion resistance. On the other hand, according to the conventional fluorinated ether compound having hydrolyzable silyl groups at both terminals, lubricity and abrasion resistance of the surface layer are insufficient.

$((R^{f1}O)_{m1})$ $R^{f1}$ may be a perfluoroalkylene group having no branched structure, or a fluoroalkylene group containing at least one hydrogen atom and having no branched structure.

As $R^{f1}$, from the viewpoint of further excellency in abrasion resistance and fingerprint stain removability of the surface layer, a $C_{1-6}$ fluoroalkylene group having no branched structure is preferred, a $C_{1-4}$ fluoroalkylene group having no branched structure is more preferred, and from the viewpoint of further excellency in lubricity of the surface layer, particularly preferred is a $C_{1-2}$ fluoroalkylene group having no branched structure.

The compound (1) has $(R^{f1}O)_{m1}$, and thus, the content of fluorine atoms is large. Therefore, it is possible to form a surface layer excellent in water/oil repellency, abrasion resistance and fingerprint stain removability.

Further, since $R^{f1}$ is a fluoroalkylene group having no branched structure, $(R^{f1}O)_{m1}$ becomes a linear structure. According to the compound (1) of such a structure, the surface layer will be excellent in abrasion resistance and lubricity. On the other hand, according to the conventional fluorinated ether compound wherein a poly(oxyperfluoroalkylene) chain has a branched structure, abrasion resistance and lubricity of the surface layer are insufficient.

m1 is an integer of from 2 to 210, preferably an integer of from 5 to 160, particularly preferably an integer of from 10 to 110. When m1 is at least the lower limit value in the above range, water/oil repellency of the surface layer will be excellent. When m1 is at most the upper limit value in the above range, abrasion resistance of the surface layer will be excellent. That is, if the number average molecular weight of the compound (1) is too large, the number of hydrolyzable silyl groups present per unit molecular weight decreases, whereby abrasion resistance decreases.

In $(R^{f1}O)_{m1}$, in a case where at least two types of $R^{f1}O$ are present, the bonding order of such plural types of $R^{f1}O$ is not limited. For example, in a case where two types of $R^{f1}O$ are present, such two types of $R^{f1}O$ may be arranged randomly, alternately or in blocks.

At least two types of $R^{f1}O$ being present is meant that in a case where $R^{f1}$ is a perfluoroalkylene group, at least two types of $R^{f1}O$ different in the number of carbon atoms are present. In a case where $R^{f1}$ is a fluoroalkylene group having hydrogen atoms, it is meant that at least two types of $R^{f1}O$ different in at least one of the number of carbon atoms, the number of hydrogen atoms and the bonding positions of hydrogen atoms, are present.

With respect to the arrangement of at least two types of $R^{f1}O$, for example in the case of fluorinated ether compounds in Examples, the structure represented by $\{(CF_2O)_{x1}(CF_2CF_2O)_{x2}\}$ indicates that x1 pieces of $(CF_2O)$ and x2 pieces of $(CF_2CF_2O)$ are randomly arranged. Further, the structure represented by $(CF_2CF_2O-CF_2CF_2CF_2CF_2O)_{x3}$ indicates that x3 pieces of $(CF_2CF_2O)$ and x3 pieces of $(CF_2CF_2CF_2CF_2O)$ are arranged alternately.

($Q^1$ Group)

$Q^1$ may be a single bond, a perfluoroalkylene group having no branched structure, or a fluoroalkylene group containing at least one hydrogen atom and having no branched structure. According to the compound (1) wherein $Q^1$ has no branched structure, it is possible to form a surface layer excellent in abrasion resistance and lubricity.

$Q^1$ may be a fluoroalkylene group derived from $R^{f1}$, or a fluoroalkylene group derived from a compound (e.g. later-described compound (30)) having an amide group and a hydrolyzable silyl group used in preparing the compound (1).

When $Q^1$ is not a single bond, the number of carbon atoms is preferably from 1 to 10.

$([C(O)N(R^1)]_{p1}$ Group)

When p1 is 0 or 1, there is no substantial difference in characteristics of the fluorinated ether compound. When p1 is 1, the compound has an amide bond, but since at least one fluorine atom is bonded to the terminal carbon atom of $Q^1$ on the side bonded to $[C(O)N(R^1)]$, the polarity of the amide bond tends to be small, and the water/oil repellency of the surface layer is less likely to be low. Whether p1 should be 0 or 1, may be selected from the viewpoint of the production efficiency.

$R^1$ in the $[C(O)N(R^1)]_{p1}$ group is, from the viewpoint of production efficiency of the compound (1), preferably a hydrogen atom.

When $R^1$ is an alkyl group, such an alkyl group is preferably a $C_{1-4}$ alkyl group. ($R^{11}$ group)

As $R^{11}$, a single bond, a $C_{1-10}$ alkylene group, a $C_{1-10}$ alkylene group having an etheric oxygen atom at its terminal (which is the terminal on the side bonded to $C[-R^{12}-SiR^{13}{}_{n1}X^1{}_{3-n1}]_3$), a $C_{2-10}$ alkylene group having an etheric oxygen atom between its carbon-carbon atoms, or a $C_{2-10}$ alkylene group having an etheric oxygen atom between its carbon-carbon atoms and at its terminal (which is the terminal on the side bonded to $C[-R^{12}-SiR^{13}{}_{n1}X^1{}_{3-n1}]_3$), is preferred.

When p1 is 0, $R^{11}$ is, from the viewpoint of production efficiency of the compound (1), preferably a single bond or an alkylene group having at most 4 carbon atoms, more preferably a single bond, a methylene group or a dimethylene group. The group having an etheric oxygen atom may, for example, be $-CH_2CH_2O-$, $-CH_2CH_2OCH_2-$, etc.

When p1 is 1, $R^{11}$ is, from the viewpoint of production efficiency of the compound (1), preferably a single bond or an alkylene group having at most 4 carbon atoms, more preferably a single bond, a methylene group or a dimethylene group.
($R^{12}$ Group)

As $R^{12}$, a $C_{1-10}$ alkylene group, a $C_{1-10}$ alkylene group having an etheric oxygen atom at its terminal (but excluding the terminal on the side bonded to Si), or a $C_{2-10}$ alkylene group having an etheric oxygen atom between its carbon-carbon atoms. From the viewpoint of production efficiency of the compound (1), a group selected from the group consisting of $-CH_2CH_2-$, $-CH_2CH_2CH_2-$, $-CH_2OCH_2CH_2CH_2-$, $-CH_2OCH_2CH_2CH_2CH_2CH_2-$ and $-OCH_2CH_2CH_2-$ (provided that the right hand side is bonded to Si), is preferred.

As $R^{12}$, from the viewpoint of excellent light resistance of the surface layer, one having no etheric oxygen atom is particularly preferred. In a touch panel for outdoor use (digital signage of vending machines, guide plates, etc.), a touch panel mounted on a vehicle or the like, the surface layer is required to have light resistance.

Three $R^{12}$ in the compound (1) may be all the same group, or may not be all the same group.
($SiR^{13}{}_{n1}X^1{}_{3-n1}$ Group)

$SiR^{13}{}_{n1}X^1{}_{3-n1}$ is a hydrolyzable silyl group.

The compound (1) has three hydrolyzable silyl groups at its terminal. The compound (1) of such a structure is chemically firmly bonded to a substrate, whereby the surface layer is excellent in abrasion resistance.

Further, the compound (1) has hydrolyzable silyl groups only at one terminal. The compound (1) of such a structure tends to be hardly agglomerated, so that the surface layer will be excellent in outer appearance.

$X^1$ is a hydrolyzable group. The hydrolyzable group is a group which becomes a hydroxy group by a hydrolysis reaction. That is, $Si-X^1$ at the terminal of the compound (1) becomes a silanol group (Si—OH) by a hydrolysis reaction. Silanol groups are further intermolecularly reacted to form Si—O—Si bonds. Further, a silanol group will be reacted for dehydration condensation with a hydroxy group (substrate-OH) at the surface of the substrate, to form a chemical bond (substrate-O—Si).

$X^1$ may, for example, be an alkoxy group, a halogen atom, an acyl group, an isocyanate group (—NCO), etc. The alkoxy group is preferably a $C_{1-4}$ alkoxy group.

As $X^1$, from the viewpoint of production efficiency of the compound (1), a $C_{1-4}$ alkoxy group or a halogen atom is preferred. As the halogen atom, a chlorine atom is particularly preferred. As $X^1$, from such a viewpoint that outgassing is less during coating, and storage stability of the compound (1) is excellent, a $C_{1-4}$ alkoxy group is preferred; in a case where long-term storage stability of the compound (1) is required, an ethoxy group is particularly preferred; and in order to shorten the reaction time after coating, a methoxy group is particularly preferred.

$R^{13}$ is a hydrogen atom or a monovalent hydrocarbon group. The monovalent hydrocarbon group may, for example, be an alkyl group, a cycloalkyl group, an alkenyl group, an allyl group, etc.

As $R^{13}$, a monovalent hydrocarbon group is preferred, and a monovalent saturated hydrocarbon group is particularly preferred. The number of carbon atoms in the monovalent saturated hydrocarbon group is preferably from 1 to 6, more preferably from 1 to 3, particularly preferably 1 or 2. When the number of carbon atoms in $R^{13}$ is within such a range, it is easy to produce the compound (1).

n1 is preferably 0 or 1, and 0 is particularly preferred. By the presence of a plurality of $X^1$ in one hydrolyzable silyl group, adhesion to the substrate becomes stronger.

As $SiR^{13}{}_{n1}X^1{}_{3-n1}$, $Si(OCH_3)_3$, $SiCH_3(OCH_3)_2$, $Si(OCH_2CH_3)_3$, $SiCl_3$, $Si(OCOCH_3)_3$, or $Si(NCO)_3$ is preferred. From the viewpoint of handling efficiency in industrial production, $Si(OCH_3)_3$ is particularly preferred.

Three $SiR^{13}{}_{n1}X^1{}_{3-n1}$ in the compound (1) may be all the same group, or may not be all the same group. From the viewpoint of production efficiency of the compound (1), it is preferred that all are the same group.
(Preferred Form of Compound (1))

As the compound (1), from such a viewpoint that abrasion resistance and fingerprint stain removability of the surface layer will be further improved, a compound (1-1) is preferred.

$$A^1-O-(R^{f5}O)_{m5}(R^{F1}O)_{m10}(R^{f5}O)_{m6}-Q^1-[C(O)N(R^1)]_{p1}-R^{11}-C[-R^{12}-SiR^{13}{}_{n1}X^1{}_{3-n1}]_3 \quad (1\text{-}1)$$

wherein $A^1$, $Q^1$, $R^1$, p1, $R^{11}$, $R^{12}$, $R^{13}$, $X^1$ and n1 are the same as in the formula (1), $R^{F1}$ is a perfluoroalkylene group having no branched structure, m10 is an integer of at least 2, and $(R^{F1}O)_{m10}$ may be one composed of at least two types of $R^{F1}O$, $R^{f5}$ is a fluoroalkylene group containing at least one hydrogen atom and having no branched structure, m5 is an integer of from 0 to 4, and when m5 is an integer of from 2 to 4, $(R^{f5}O)_{m5}$ may be one composed of at least two types of $R^{f5}O$, $R^{f6}$ is a fluoroalkylene group containing at least one hydrogen atom and having no branched structure, m6 is an integer of from 0 to 4, and when m6 is an integer of from 2 to 4, $(R^{f6}O)_{m6}$ may be one composed of at least two types of $R^{f6}O$, and m10+m5+m6=m1.
$((R^{f5}O)_{m5})$ $R^{f5}$ is a fluoroalkylene group containing at least one hydrogen atom and having no branched structure, preferably a $C_{2-6}$ fluoroalkylene group, particularly preferably a $C_2$ fluoroalkylene group. The number of hydrogen atoms is preferably from 1 to 4, particularly preferably 1 or 2. As $(R^{f5}O)$, $(CHFCF_2O)$ and $(CH_2CF_2O)$ are preferred.

m5 is preferably an integer of from 0 to 2, more preferably 0 or 2. When m is 2, $(R^{f5}O)_2$ is preferably $(CHFCF_2O)-(CH_2CF_2O)$.

$((R^{F1}O)_{m10})$

As $R^{F1}$, from such a viewpoint that abrasion resistance and fingerprint stain removability of the surface layer will be further improved, a $C_{1-6}$ perfluoroalkylene group having no branched structure is preferred, and a $C_{1-4}$ perfluoroalkylene group having no branched structure is more preferred; and from such a viewpoint that lubricity of the surface layer will be further improved, a $C_{1-2}$ perfluoroalkylene group having no branched structure is particularly preferred.

Since the compound (1-1) has $(R^{F1}O)_{m10}$, the content of fluorine atoms is higher. Therefore, it is possible to form a surface layer further excellent in water/oil repellency, abrasion resistance and fingerprint stain removability.

Further, since $R^{F1}$ is a perfluoroalkylene group having no branched structure, $(R^{F1}O)_{m10}$ becomes to have a straight chain structure. According to the compound (1-1) of such a structure, abrasion resistance and lubricity of the surface layer will be excellent.

In $(R^{F1}O)_{m10}$, when at least two types of $R^{F1}O$ different in number of carbon atoms are present, the bonding order of such plural types of $R^{F1}O$ is not limited. For example, when $CF_2O$ and $CF_2CF_2O$ are present, such $CF_2O$ and $CF_2CF_2O$ may be arranged randomly, alternately or in block.

As $(R^{F1}O)_{m10}$, from such a viewpoint that the surface layer will be further excellent in abrasion resistance, fingerprint stain removability and lubricity, $(CF_2O)_{m11}(CF_2CF_2O)_{m12}$, $(CF_2CF_2O)_{m13}$, $(CF_2CF_2CF_2O)_{m14}$, or $(CF_2CF_2O-CF_2CF_2CF_2CF_2O)_{m15}$ is preferred, and $(CF_2O)_{m11}(CF_2CF_2O)_{m12}$ is particularly preferred.

Here, m11 is an integer of at least 1, m12 is an integer of at least 1, and the bonding order of m11 pieces of $CF_2O$ and m12 pieces of $CF_2CF_2O$ is not limited. Preferred is a randomly arranged structure represented by $\{(CF_2O)_{m11}(CF_2CF_2O)_{m12}\}$. m13 and m14 are each an integer of from 2 to 200, and m15 is an integer of from 1 to 100.

$((R^{f6}O)_{m6})$ $R^{f6}$ is a fluoroalkylene group containing at least one hydrogen atom and having no branched structure, preferably a $C_{2-6}$ fluoroalkylene group. The number of hydrogen atoms is preferably from 1 to 4, particularly preferably 1 or 2. m6 is preferably from 0 to 2.

In a case where p1 is 0, $Q^1$ is preferably a single bond. In such a case (i.e. a case where $(R^{f6}O)_{m6}$ and $R^{11}$ are directly bonded), in $(R^{f6}O)_{m6}$, $(R^{f6}O)$ bonding directly to $R^{11}$ is preferably a group represented by $(R^{f7}CH_2O)$. $R^{f7}$ is a group having the number of carbon atoms less by one than $R^{f6}$, and is a perfluoroalkylene group or a fluoroalkylene group having hydrogen atom(s). $R^{f7}$ is preferably a perfluoroalkylene group. As specific $(R^{f7}CH_2O)$, $(CF_2CH_2O)$, $(CF_2CF_2CH_2O)$, $(CF_2CF_2CF_2CH_2O)$, $(CF_2CF_2CF_2CF_2CH_2O)$, etc. are preferred. In such a case, m6 is preferably 1.

In a case where p1 is 1, it is preferred that m6 is from 0 to 2, and $Q^1$ is a fluoroalkylene group. In such a case, $Q^1$ is preferably a perfluoroalkylene group. The number of carbon atoms in $Q^1$ being a perfluoroalkylene group is more preferably from 1 to 6.

m10+m5+m6 is an integer of from 2 to 200, preferably an integer of from 5 to 150, particularly preferably an integer of from 10 to 110. When m10+m5+m6 is at least the lower limit value in the above range, the surface layer will be excellent in water/oil repellency. When m10+m5+m6 is at most the upper limit value in the above range, the surface layer will be excellent in abrasion resistance. That is, if the number average molecular weight of the compound (1-1) is too large, the number of hydrolyzable silyl groups present per unit molecular weight decreases, whereby the abrasion resistance decreases.

M10 is more preferably an integer of at least 5, particularly preferably at least 10.

(Preferred Form of Compound (1-1))

As the compound (1-1), for example, compounds of the following formulae may be mentioned. Such compounds are preferred from such a viewpoint that it is easy to produce them industrially, it is easy to handle them, and the surface layer will be further excellent in water/oil repellency, abrasion resistance, fingerprint stain removability, lubricity and outer appearance.

Compound (1-1) wherein $Q^1$ is a single bond and p1=0.

Here, in the following formulae, "PFPE-CH$_2$O—" and other "PFPE-" represent $A^1$-O—$(R^{f5}O)_{m5}(R^{F1}O)_{m10}(R^{f6}O)_{m6}$—.

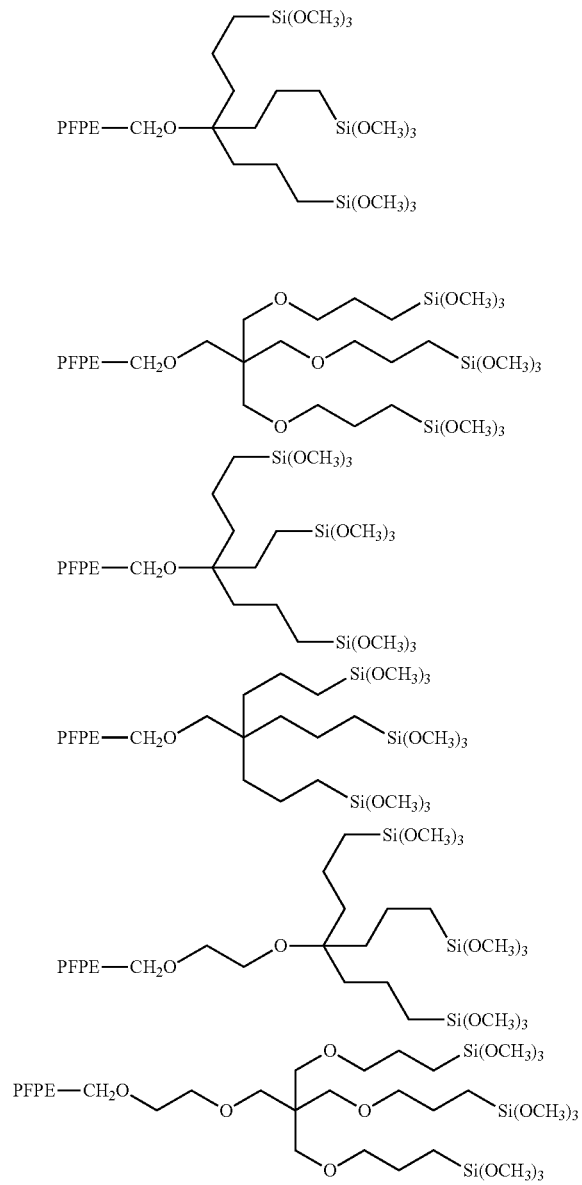

-continued

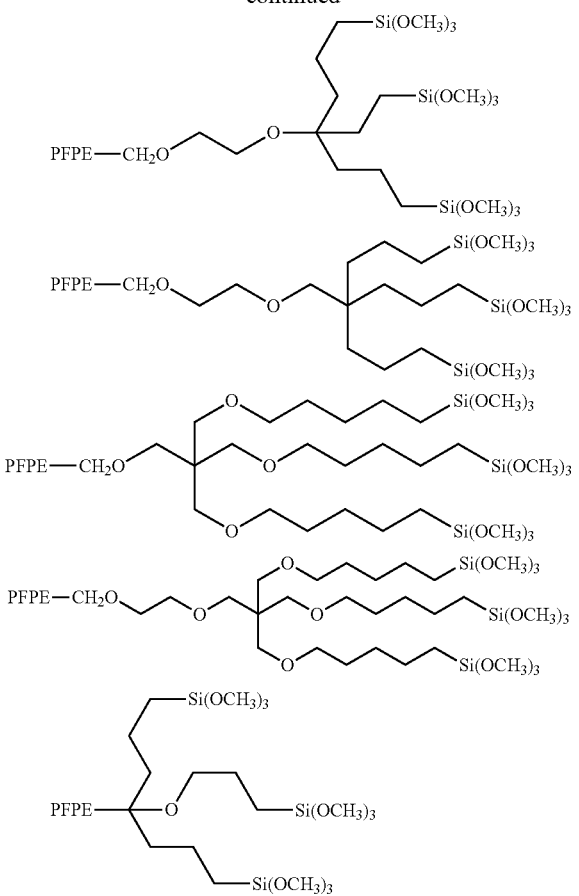

Compound (1-1) wherein $Q^1$ is a perfluoroalkylene group and p1=1

Here, in the chemical formulae, "PFPE-$R^F$—" represents $A^1$-O—$(R^{f5}O)_{m5}(R^{F1}O)_{m10}(R_{f6}O)_{m6}$-$Q^1$-.

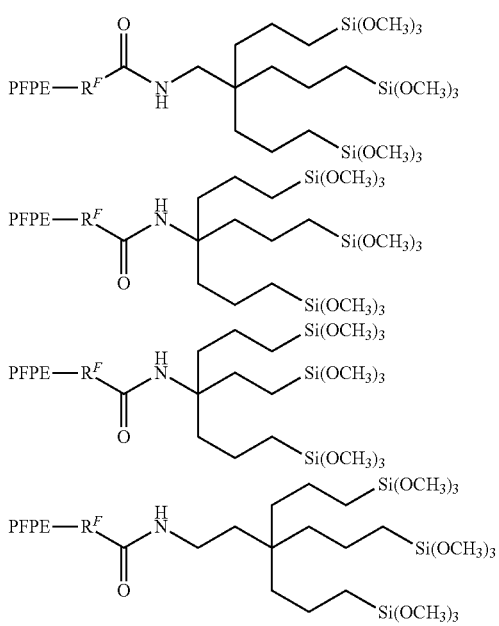

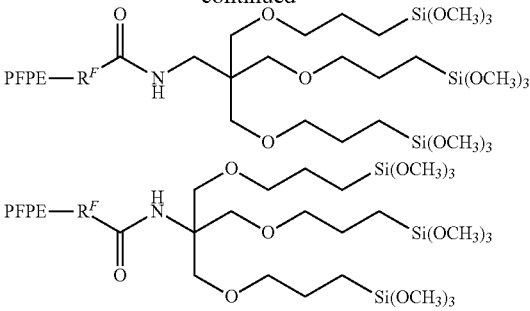

(Method for Producing Compound (1))

In a case where p1 is 0, as the method for producing the compound (1), for example, the following methods (10) to (15) may be mentioned.

In a case where p1 is 1, as the method for producing the compound (1), for example, the following methods (20) to (25) may be mentioned.

<Method (10)>

As the starting material, commercially available compound (10) is to be used.

$$\text{HO—CH}_2\text{—(CF}_2\text{O)(R}^{F1}\text{O)}_x\text{—CF}_2\text{—CH}_2\text{—OH} \quad (10)$$

In the presence of a basic compound, to the compound (10), $A^1$-O—CF=CF$_2$ is reacted to obtain a mixture of compound (11), compounds (3A) and unreacted compound (10).

$$A^1\text{-O—CHFCF}_2\text{OCH}_2\text{—(CF}_2\text{O)(R}^{F1}\text{O)}_x\text{—CF}_2\text{—CH}_2\text{—OH} \quad (11)$$

$$A^1\text{-O—CHFCF}_2\text{OCH}_2\text{—(CF}_2\text{O)(R}^{F1}\text{O)}_x\text{—CF}_2\text{—CH}_2\text{OCF}_2\text{CHF—O-A}^1 \quad (3A)$$

From the mixture, the compound (11) is isolated, and the compound (11) and CF$_3$CF$_2$CF$_2$OCF(CF$_3$)C(O)F are subjected to an esterification reaction to obtain compound (12). The esterification reaction may be a reaction of the compound (1) with other acid fluoride, acid chloride, acid bromide, acid anhydride or the like.

$$A^1\text{-O—CHFCF}_2\text{OCH}_2\text{—(CF}_2\text{O)(R}^{F1}\text{O)}_x\text{—CF}_2\text{—CH}_2\text{—OC(O)CF(CF}_3\text{)OCF}_2\text{CF}_2\text{CF}_3 \quad (12)$$

By using fluorine gas, hydrogen atoms in the compound (12) are substituted by fluorine atoms to obtain compound (13). The fluorination step may, for example, be carried out in accordance with the method described in WO2000/56694.

$$A^1\text{-O—(CF}_2\text{CF}_2\text{O)(CF}_2\text{CF}_2\text{O)(R}^{F1}\text{O)}_x(\text{CF}_2\text{CF}_2\text{O)—C(O)CF(CF}_3\text{)OCF}_2\text{CF}_2\text{CF}_3 \quad (13)$$

To the compound (13), an alcohol (methanol, ethanol, 1-propanol, 2-propanol, etc.; hereinafter referred to as $R^{10}$OH, where $R^{10}$ is an alkyl group) is reacted to obtain compound (14).

$$A^1\text{-O—(CF}_2\text{CF}_2\text{O)(CF}_2\text{CF}_2\text{O)(R}^{F1}\text{O)}_x\text{—CF}_2\text{—C(O)OR}^{10} \quad (14)$$

The compound (14) is subjected to hydrogen reduction by using a reducing agent sodium borohydride, lithium aluminum hydride, etc.) to obtain compound (15).

$$A^1\text{-O—(CF}_2\text{CF}_2\text{O)(CF}_2\text{CF}_2\text{O)(R}^{F1}\text{O)}_x\text{—CF}_2\text{—CH}_2\text{OH} \quad (15)$$

In the presence of a basic compound, to the compound (15), CF$_3$SO$_2$Cl is reacted to obtain compound (16).

$$A^1\text{-O—(CF}_2\text{CF}_2\text{O)(CF}_2\text{CF}_2\text{O)(R}^{F1}\text{O)}_x\text{—CF}_2\text{—CH}_2\text{OSO}_2\text{CF}_3 \quad (16)$$

In the presence of a basic compound, to the compound (16), $HOCH_2C(CH_2OCH_2CH=CH_2)_3$ is reacted to obtain compound (17).

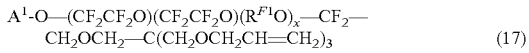

(17)

The compound (17) and $HSiR^{13}{}_{n1}X^{1}{}_{3-n1}$ are subjected to a hydrosilylation reaction to obtain compound (1A). The hydrosilylation reaction is preferably carried out by using a transition metal catalyst such as platinum or a radical generator such as an organic peroxide.

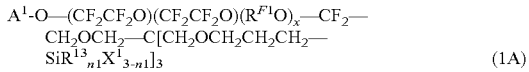

(1A)

Here, when the above formula is summarized in the order of oxyfluoroalkylene units, the compound (1A) is represented by the following formula.

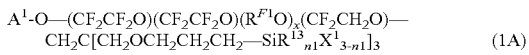

(1A)

<Method (11)>

As the starting material, the compound (11) obtained in the method (10) is to be used.

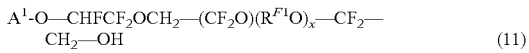

(11)

In the presence of a basic compound, to the compound (11), $CF_3SO_2Cl$ is reacted to obtain compound (16B).

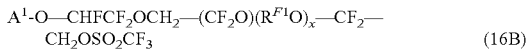

(16B)

In the presence of a basic compound, to the compound (16B), $HOCH_2C(CH_2OCH_2CH=CH_2)_3$ is reacted to obtain compound (17B).

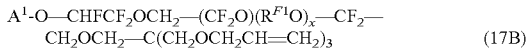

(17B)

The compound (17B) and $HSiR^{13}{}_{n1}X^{1}{}_{3-n1}$ are subjected to a hydrosilylation reaction to obtain compound (16).

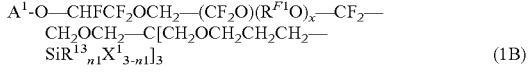

(1B)

Here, when the above formula is summarized in the order of oxyfluoroalkylene units, the compound (1B) is represented by the following formula.

(1B)

<Method (12)>

As the starting material, compound (15C) obtained by the method described in WO2013/121984 is to be used.

(15C)

wherein $Q^{12}$ is a perfluoroalkylene group having no branched structure.

In the presence of a basic compound, to the compound (15C), $CF_3SO_2Cl$ is reacted to obtain compound (16C).

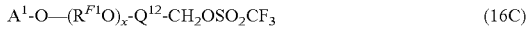

(16C)

In the presence of a basic compound, to the compound (16C), $HOCH_2C(CH_2OCH_2CH=CH_2)_3$ is reacted to obtain compound (17C).

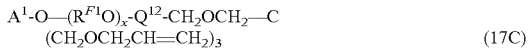

(17C)

The compound (17C) and $HSiR^{13}{}_{n1}X^{1}{}_{3-n1}$ are subjected to a hydrosilylation reaction to obtain compound (1C).

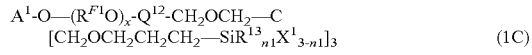

(1C)

Here, when the above formula is summarized in the order of oxyfluoroalkylene units, the compound (1C) is represented by the following formula.

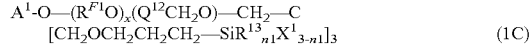

(1C)

<Method (13)>

$HOCH_2C(CH_2CH=CH_2)_3$ and $(CF_3SO_2)_2O$ are reacted to obtain compound (20).

$CF_3SO_2OCH_2C(CH_2CH=CH_2)_3$ (20)

As the starting material, the compound (15) obtained in the method (10) is to be used.

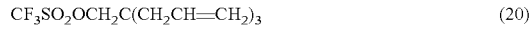

(15)

wherein x is an integer of from 1 to 198.

In the presence of a basic compound, the compound (20) is reacted to the compound (15) to obtain compound (17D).

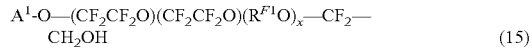

(17D)

The compound (17D) and $HSiR^{13}{}_{n1}X^{1}{}_{3-n1}$ are subjected to a hydrosilylation reaction to obtain compound (1D).

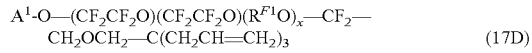

(1D)

Here, when the above formula is summarized in the order of oxyfluoroalkylene units, the compound (1 D) is represented by the following formula.

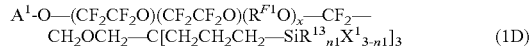

(1D)

<Method (14)>

As the starting material, the compound (11) obtained in the method (10) is to be used.

(11)

In the presence of a basic compound, to the compound (11), the compound (20) obtained in the method (13) is reacted to obtain compound (17E).

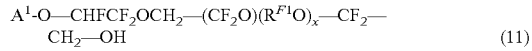

(17E)

The compound (17E) and $HSiR^{13}{}_{n1}X^{1}{}_{3-n1}$ are subjected to a hydrosilylation reaction to obtain compound (1E).

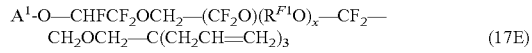

(1E)

Here, when the above formula is summarized in the order of oxyfluoroalkylene units, the compound (1E) is represented by the following formula.

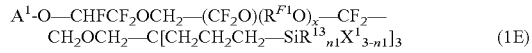

(1E)

<Method (15)>

As the starting material, compound (15C) obtained by the method described in WO2013/121984 is to be used.

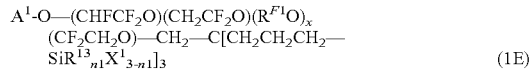

(15C)

wherein Q12 is a perfluoroalkylene group having no branched structure.

In the presence of a basic compound, to the compound (15C), the compound (20) obtained in the method (13) is reacted to obtain compound (17F).

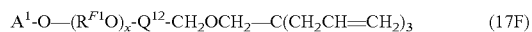

(17F)

The compound (17F) and $HSiR^{13}{}_{n1}X^1{}_{3-n1}$ are subjected to a hydrosilylation reaction to obtain compound (1F).

$$A^1\text{-O}-(R^{F1}O)_x\text{-}Q^{12}\text{-}CH_2OCH_2\text{—}C[CH_2CH_2CH_2\text{—}SiR^{13}{}_{n1}X^1{}_{3-n1}]_3 \quad (1F)$$

Here, when the above formula is summarized in the order of oxyfluoroalkylene units, the compound (1F) is represented by the following formula.

$$A^1\text{-O}-(R^{F1}O)_x(Q^{12}CH_2O)\text{—}CH_2\text{—}C[CH_2CH_2CH_2\text{—}SiR^{13}{}_{n1}X^1{}_{3-n1}]_3 \quad (1F)$$

<Method (20)>

As the starting material, the compound (14) obtained in the method (10) is to be used.

$$A^1\text{-O}-(CF_2CF_2O)(CF_2CF_2O)(R^{F1}O)_x\text{—}CF_2\text{—}C(O)OR^{10} \quad (14)$$

To the compound (14), $H_2N\text{—}R^{11}\text{—}C(CH_2CH=CH_2)_3$ is reacted to obtain compound (17G).

$$A^1\text{-O}-(CF_2CF_2O)(CF_2CF_2O)(R^{F1}O)_x\text{—}CF_2\text{—}C(O)NH\text{—}R^{11}\text{—}C(CH_2CH=CH_2)_3 \quad (17G)$$

The compound (17G) and $HSiR^{13}{}_{n1}X^1{}_{3-n1}$ are subjected to a hydrosilylation reaction to obtain compound (1 G).

$$A^1\text{-O}-(CF_2CF_2O)(CF_2CF_2O)(R^{F1}O)_x\text{—}CF_2\text{—}C(O)NH\text{—}R^{11}\text{—}C[CH_2CH_2CH_2\text{—}SiR^{13}{}_{n1}X^1{}_{3-n1}]_3 \quad (1G)$$

<Method (21)>

As the starting material, the compound (11) obtained in the method (10) is to be used.

$$A^1\text{-O}\text{—}CHFCF_2OCH_2\text{—}(CF_2O)(R^{F1}O)_x\text{—}CF_2\text{—}CH_2\text{—}OH \quad (11)$$

In accordance with the method described in J. Org. Chem., Vol. 64, 1999, p. 2564-2566, the compound (11) is oxidized to obtain compound (13H).

$$A^1\text{-O}\text{—}CHFCF_2OCH_2\text{—}(CF_2O)(R^{F1}O)_x\text{—}CF_2\text{—}C(O)OH \quad (13H)$$

To the compound (13H), $R^{10}OH$ is reacted to obtain compound (14H).

$$A^1\text{-O}\text{—}CHFCF_2OCH_2\text{—}(CF_2O)(R^{F1}O)_x\text{—}CF_2\text{—}C(O)OR^{10} \quad (14H)$$

To the compound (14H), $H_2N\text{—}R^{11}\text{—}C(CH_2CH=CH_2)_3$ is reacted to obtain compound (17H).

$$A^1\text{-O}\text{—}CHFCF_2OCH_2\text{—}(CF_2O)(R^{F1}O)_x\text{—}CF_2\text{—}C(O)NH\text{—}R^{11}\text{—}C(CH_2CH=CH_2)_3 \quad (17H)$$

The compound (17H) and $HSiR^{13}{}_{n1}X^1{}_{3-n1}$ are subjected to a hydrosilylation reaction to obtain compound (1H).

$$A^1\text{-O}\text{—}CHFCF_2OCH_2\text{—}(CF_2O)(R^{H}O)_x\text{—}CF_2\text{—}C(O)NH\text{—}R^{11}\text{—}C[CH_2CH_2CH_2\text{—}SiR^{13}{}_{n1}X^1{}_{3-n1}]_3 \quad (1H)$$

Here, when the above formula is summarized in the order of oxyfluoroalkylene units, the compound (1H) is represented by the following formula.

$$A^1\text{-O}-(CHFCF_2O)(CH_2CF_2O)(R^{F1}O)_x\text{—}CF_2\text{—}C(O)NH\text{—}R^{11}\text{—}C[CH_2CH_2CH_2\text{—}SiR^{13}{}_{n1}X^1{}_{3-n1}]_3 \quad (1H)$$

<Method (22)>

As the starting material, compound (14I) obtained by the method described in WO2013/121984 is to be used.

$$A^1\text{-O}-(R^{F1}O)_x\text{-}Q^{12}\text{-}C(O)OR^{10} \quad (14I)$$

wherein $Q^{12}$ is a perfluoroalkylene group having no branched structure.

To the compound (14I), $H_2N\text{—}R^{11}\text{—}C(CH_2CH=CH_2)_3$ is reacted to obtain compound (17I).

$$A_1\text{-O}-(R^{F1}O)_x\text{-}Q^{12}\text{-}C(O)NH\text{—}R^{11}\text{—}C(CH_2CH=CH_2)_3 \quad (17I)$$

The compound (17I) and $HSiR^{13}{}_{n1}X^1{}_{3-n1}$ are subjected to a hydrosilylation reaction to obtain compound (1I).

$$A^1\text{-O}-(R^{F1}O)_x\text{-}Q^{12}\text{-}C(O)NH\text{—}R^{11}\text{—}C[CH_2CH_2CH_2\text{—}SiR^{13}{}_{n1}X^1{}_{3-n1}]_3 \quad (1I)$$

<Method (23)>

$CF_2=CFOCF_2CF_2CF_2\text{—}C(O)OCH_3$ and $H_2N\text{—}R^{11}\text{—}C(CH_2CH=CH_2)_3$ are reacted to obtain compound (30).

$$CF_2=CFOCF_2CF_2CF_2\text{—}C(O)NH\text{—}R^{11}\text{—}C(CH_2CH=CH_2)_3 \quad (30)$$

As the starting material, the compound (15) obtained in the method (10) is to be used.

$$A^1\text{-O}-(CF_2CF_2O)(CF_2CF_2O)(R^{F1}O)_x\text{—}CF_2\text{—}CH_2OH \quad (15)$$

wherein x is an integer of from 1 to 198.

In the presence of a basic compound, the compound (30) is reacted to the compound (15) to obtain compound (17J).

$$A^1\text{-O}-(CF_2CF_2O)(CF_2CF_2O)(R^{F1}O)_x\text{—}CF_2CH_2OCF_2CHFOCF_2CF_2CF_2\text{—}C(O)NH\text{—}R^{11}\text{—}C(CH_2CH=CH_2)_3 \quad (17J)$$

The compound (17J) and $HSiR^{13}{}_{n1}X^1{}_{3-n1}$ are subjected to a hydrosilylation reaction to obtain compound (1J).

$$A^1\text{-O}-(CF_2CF_2O)(CF_2CF_2O)(R^{F1}O)_x\text{—}CF_2CH_2OCF_2CHFOCF_2CF_2CF_2\text{—}C(O)NH\text{—}R^{11}\text{—}C[CH_2CH_2CH_2\text{—}SiR^{13}{}_{n1}X^1{}_{3-n1}]_3 \quad (1J)$$

Here, when the above formula is summarized in the order of oxyfluoroalkylene units, the compound (1J) is represented by the following formula.

$$A^1\text{-O}-(CF_2CF_2O)(CF_2CF_2O)(R^{F1}O)_x(CF_2CH_2O)(CF_2CHFO)\text{—}CF_2CF_2CF_2\text{—}C(O)NH\text{—}R^{11}\text{—}C[CH_2CH_2CH_2\text{—}SiR^{13}{}_{n1}X^1{}_{3-n1}]_3 \quad (1J)$$

<Method (24)>

As the starting material, the compound (11) obtained in the method (10) is to be used.

$$A^1\text{-O}\text{—}CHFCF_2OCH_2\text{—}(CF_2O)(R^{F1}O)_x\text{—}CF_2\text{—}CH_2OH \quad (11)$$

In the presence of a basic compound, to the compound (11), the compound (30) obtained in the method (23) is reacted to obtain compound (17K).

$$A^1\text{-O}\text{—}CHFCF_2OCH_2\text{—}(CF_2O)(R^{F1}O)_x\text{—}CF_2CH_2OCF_2CHFOCF_2CF_2CF_2\text{—}C(O)NH\text{-}R^{11}\text{—}C(CH_2CH=CH_2)_3 \quad (17K)$$

The compound (17K) and $HSiR^{13}{}_{n1}X^1{}_{3-n1}$ are subjected to a hydrosilylation reaction to obtain compound (1K).

$$A^1\text{-O}\text{—}CHFCF_2OCH_2\text{-}(CF_2O)(R^{F1}O)_x\text{—}CF_2CH_2OCF_2CHFOCF_2CF_2CF_2\text{—}C(O)NH\text{—}R^{11}\text{—}C[CH_2CH_2CH_2\text{—}SiR^{13}{}_{n1}X^1{}_{3-n1}]_3 \quad (1K)$$

Here, when the above formula is summarized in the order of oxyfluoroalkylene units, the compound (1K) is represented by the following formula.

$$A^1\text{-O}-(CHFCF_2O)(CH_2CF_2O)(R^{F1}O)_x(CF_2CH_2O)(CF_2CHFO)\text{—}CF_2CF_2CF_2\text{—}C(O)NH\text{—}R^{11}\text{—}C[CH_2CH_2CH_2\text{—}SiR^{13}{}_{n1}X^1{}_{3-n1}]_3 \quad (1K)$$

<Method (25)>

As the starting material, compound (15C) obtained by the method described in WO02013/121984 is to be used.

$$A^1\text{-O}-(R^{F1}O)_x\text{—}R^FCH_2OH \quad (15C)$$

wherein x is an integer of from 1 to 200, and $R^F$ is a perfluoroalkylene group having no branched structure.

In the presence of a basic compound, to the compound (15C), the compound (30) obtained in the method (23) is reacted to obtain a compound (17L).

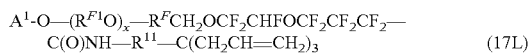

The compound (17L) and $HSiR^{13}{}_{n1}X^1{}_{3-n1}$ are subjected to a hydrosilylation reaction to obtain compound (1 L).

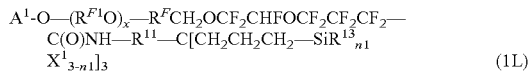

Here, when the above formula is summarized in the order of oxyfluoroalkylene units, the compound (1 L) is represented by the following formula.

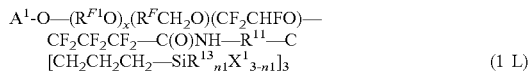

(The Present Compound)

The present compound may be a single compound composed of one type of compound (1), or a mixture composed of at least two types of compound (1) different in $A^1$, $(R^{f1}O)_{m1}$, $Q^1$, $R^1$, p1, $R^{11}$, $R^{12}$, $SiR^{13}{}_{n1}X^1{}_{3-n1}$, etc.

In the present invention, compound (1) being a single compound is meant for the same group of compounds except having a distribution in the number of m1. For example, in the case of compound (1-1), when $(R^{F1}O)_{m10}$ is $\{(CF_2O)_{m11}(CF_2CF_2O)_{m12}\}$, it is meant for the same group of compounds except having a distribution in m11 and m12 and when represented by $\{(CF_2O)_{m11/m10}(CF_2CF_2O)_{m12/m10}\}_{m10}$, it is meant for the same group of compounds except having a distribution in the number of m10. Since commercially available compound (10) is a compound which may normally be regarded as a single compound in the above sense, its derivatives having no change occurred at the $(R^{F1}O)_x$ portion can be regarded as a single compound so long as other portions ($A^1$, $Q^{11}$, $Q^{12}$, $R^1$, p1, $R^{11}$, $R^{12}$, $SiR^{13}{}_{n1}X^1{}_{3-n1}$ etc.) are the same.

The number average molecular weight of the present compound is preferably from 500 to 20,000, more preferably from 800 to 10,000, particularly preferably from 1,000 to 8,000. When the number average molecular weight is within the range, abrasion resistance will be excellent.

[Fluorinated Ether Composition]

The fluorinated ether composition of the present invention (hereinafter referred to also as the present composition) is a composition comprising compound (1), and a fluorinated ether compound other than the compound (1). The fluorinated ether compound other than the compound (1) (hereinafter referred to also as other fluorinated ether compound) may, for example, be a fluorinated ether compound by-produced in the process for producing the compound (1), a known (particularly commercially available) fluorinated ether compound to be used in the same applications as the compound (1), etc. Other fluorinated ether compound is preferably a compound which is less likely to reduce the properties of the compound (1), and its relative content to the compound (1) in the present composition is preferably in such an amount as less likely to reduce the properties of the compound (1).

In a case where other fluorinated ether compound is a fluorinated ether compound by-produced in the process for producing the compound (1), the purification of the compound (1) in the production of the compound (1) becomes easy, and the purification process can be simplified. In a case where other fluorinated ether compound is a known fluorinated ether compound to be used in the same applications as the compound (1), there may be a case where a new function or effect such as to supplement the properties of the compound (1) is exhibited.

Such other fluorinated ether compound is preferably at least one member selected from the group consisting of the following fluorinated ether compound (2), the following fluorinated ether compound (3) and the following fluorinated ether compound (4).

Fluorinated ether compound (2): A fluorinated ether compound wherein in the fluorinated ether compound represented by the formula (1), a group having said $—C[—R^{12}—SiR^{13}{}_{n1}X^1{}_{3-n1}]_3$ is bonded to both sides of said $(R^{f1}O)_{m1}$, Fluorinated ether compound (3): A fluorinated ether compound wherein in the fluorinated ether compound represented by the formula (1), a group having said $A^1$ is bonded to both sides of said $(R^{f1}O)_{m1}$, Fluorinated ether compound (4): A fluorinated ether compound wherein in the fluorinated ether compound represented by the formula (1), said $—C[—R^{12}—SiR^{13}{}_{n1}X^1{}_{3-n1}]_3$ is substituted by $—C[—R^{12}—SiR^{13}{}_{n1}X^1{}_{3-n1}]_{3-t}[—R^{15}]_t$ (wherein $R^{15}$ is an unsaturated bond-containing group which becomes $—R^{12}—SiR^{13}{}_{n1}X^1{}_{3-n1}$ by addition of $HSiR^{13}{}_{n1}X^1{}_{3-n1}$, or an isomer group of the unsaturated bond-containing group, and t is an integer of 1 to 3.).

From such a viewpoint that it is less likely to reduce the properties of the compound (1), as the fluorinated ether compound (2), the after-mentioned compound (2) is preferred, as the fluorinated ether compound (3), the after-mentioned compound (3) is preferred, and as the fluorinated ether compound (4), the after-mentioned compound (4) is preferred.

(Compound (2))

Compound (2) is a fluorinated ether compound represented by the following formula (2).

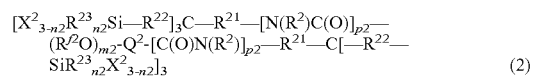

wherein $R^{f2}$ is a fluoroalkylene group having no branched structure; m2 is an integer of from 2 to 210; $(R^{f2}O)_{m2}$ may be one composed of at least two types $R^{f2}O$ different in number of carbon atoms; $Q^2$ is a fluoroalkylene group having no branched structure; $R^2$ is a hydrogen atom or an alkyl group; p2 is 0 or 1, and two p2 may not be the same number; $R^{21}$ is a single bond, an alkylene group, an alkylene group having an etheric oxygen atom at its terminal (which is the terminal on the side bonded to $[X^2{}_{3-n2}R^{23}{}_{n2}Si—R^{22}—]_3C$), an alkylene group with at least two carbon atoms having an etheric oxygen atom between its carbon-carbon atoms, or an alkylene group with at least two carbon atoms having an etheric oxygen atom between its carbon-carbon atoms and at its terminal (which is the terminal on the side bonded to $[X^2{}_{3-n2}R^{23}{}_{n2}Si—R^{22}—]_3C$), and two $R^{21}$ may not be the same group; $R^{22}$ is an alkylene group, an alkylene group having an etheric oxygen atom at its terminal (but excluding the terminal on the side bonded to Si), or an alkylene group with at least two carbon atoms having an etheric oxygen atom between its carbon-carbon atoms; $R^{23}$ is a hydrogen atom or a monovalent hydrocarbon group; $X^2$ is a hydrolyzable group; n2 is an integer of from 0 to 2; and six $[—R^{22}—SiR^{23}{}_{n2}X^2{}_{3-n2}]$ may not be all the same group.

$(R^{f2}O)_{m2}$, $Q^2$, $R^2$, p2, $R^{21}$, $R^{22}$ and $SiR^{23}{}_{n2}X^2{}_{3-n2}$ may, respectively, be the same as $(R^{f1}O)_{m1}$, $Q^1$, $R^1$, p1, $R^{11}$, $R^{12}$ and $SiR^{13}{}_{n1}X^1{}_{3-n1}$ in compound (1), and their preferred examples are also the same.

In a case where p2 is 0 and $R^{f2}$ is a fluoroalkylene group containing at least two hydrogen atoms and having no branched structure, and further, no etheric oxygen atom exists at the terminal of $R^{21}$ on the side bonded to $R^{f2}$, at least one fluorine atom is bonded to the carbon atom at the terminal of $R^{f2}$ on the side bonded to $R^{21}$.

In a case where p2 is 0 and $Q^2$ is a fluoroalkylene group containing at least two hydrogen atoms and having no branched structure, and further, no etheric oxygen atom exists at the terminal of $R^{21}$ on the side bonded to $Q^2$, at least one fluorine atom is bonded to the carbon atom at the terminal of $Q^2$ on the side bonded to $R^{21}$.

(Preferred Form of Compound (2))

As the compound (2), from such a viewpoint that the surface layer will be further excellent in abrasion resistance and fingerprint stain removability, compound (2-1) is preferred.

$$[X^2{}_{3-n2}R^{23}{}_{n2}Si{-}R^{22}{-}]_3C{-}R^{21}{-}[N(R^2)C(O)]_{p2}{-}Q^{21}{-}(R^{f2}O)_{m20}{-}Q^{22}{-}[C(O)N(R^2)]_{p2}{-}R^{21}{-}C[{-}R^{22}{-}SiR^{23}{}_{n2}X^2{}_{3-n2}]_3 \quad (2\text{-}1)$$

wherein $R^2$, p2, $R^{21}$, $R^{22}$, $R^{23}$, $X^2$ and n2 are the same as in the above formula (2); $Q^{21}$ is a single bond, a fluoroalkylene group containing at least one hydrogen atom and having no branched structure, a fluoroalkylene group containing at least one hydrogen atom and having no branched structure, which has an etheric oxygen atom at its terminal (but excluding the terminal on the side bonded to C(O)), a fluoroalkylene group with at least two carbon atoms containing at least one hydrogen atom and having no branched structure, which has an etheric oxygen atom between its carbon-carbon atoms, or a fluoroalkylene group with at least two carbon atoms containing at least one hydrogen atom and having no branched structure, which has an etheric oxygen atom between its carbon-carbon atoms and at its terminal (but excluding the terminal on the side bonded to C(O)) (provided that the number of oxygen atoms is at most 10); $R^{f2}$ is a perfluoroalkylene group having no branched structure; m20 is an integer of from 2 to 200; $(R^{f2}O)_{m20}$ may be one composed of at least two types of $R^{f2}O$ different in number of carbon atoms; $Q^{22}$ is a perfluoroalkylene group having no branched structure, a fluoroalkylene group containing at least one hydrogen atom and having no branched structure, or a fluoroalkylene group with at least two carbon atoms containing at least one hydrogen atom and having no branched structure, which has an etheric oxygen atom between its carbon-carbon atoms.

$Q^{21}$, $(R^{f2}O)_{m20}$ and $Q^{22}$ may, respectively, be the same as $Q^{11}$, $(R^{f1}O)_{m10}$ and $Q^{12}$ in the compound (1-1), and their preferred examples are also the same.

In a case where $Q^{21}$ is a fluoroalkylene group containing at least one hydrogen atom and having no branched structure, or a fluoroalkylene group with at least two carbon atoms containing at least one hydrogen atom and having no branched structure, which has an etheric oxygen atom between its carbon-carbon atoms, and no etheric oxygen atom exists at the terminal of $Q^{21}$ on the side bonded to $(R^{f2}O)_{m20}$, at least one hydrogen atom is bonded to the carbon atom at the terminal of $Q^{21}$ on the side bonded to $(R^{f2}O)_{m20}$.

(Method for Producing Compound (2))

In a case where p2 is 0, as the method for producing the compound (2), for example, the following methods (30) and (31) may be mentioned.

In a case where p2 is 1, as the method for producing the compound (2), for example, the following methods (40) and (41) may be mentioned.

<Method (30)>

As the starting material, commercially available compound (10) is to be used.

$$HO{-}CH_2{-}CF_2O(R^{f2}O)_x{-}CF_2{-}CH_2{-}OH \quad (10)$$

wherein x is an integer of from 1 to 199.

In the presence of a basic compound, to the compound (10), $CF_3SO_2Cl$ is reacted to obtain compound (18).

$$CF_3SO_2OCH_2{-}(CF_2O)(R^{f2}O)_x{-}CF_2{-}CH_2OSO_2CF_3 \quad (18)$$

In the presence of a basic compound, to the compound (18), $HOCH_2C(CH_2OCH_2CH{=}CH_2)_3$ is reacted to obtain compound (19).

$$(CH_2{=}CHCH_2OCH_2)_3C{-}CH_2OCH_2{-}(CF_2O)(R^{f2}O)_x{-}CF_2{-}CH_2OCH_2{-}C(CH_2OCH_2CH{=}CH_2)_3 \quad (19)$$

The compound (19) and $HSiR^{23}{}_{n2}X^2{}_{3-n2}$ are subjected to a hydrosilylation reaction to obtain compound (2A).

$$[X^2{}_{3-n2}R^{23}{}_{n2}Si{-}CH_2CH_2CH_2OCH_2]_3C{-}CH_2OCH_2{-}(CF_2O)(R^{f2}O)_x{-}CF_2{-}CH_2OCH_2{-}C[CH_2OCH_2CH_2CH_2{-}SiR^{23}{}_{n2}X^2{}_{3-n2}]_3 \quad (2A)$$

<Method (31)>

As the starting material, commercially available compound (10) is to be used.

$$HO{-}CH_2{-}(CF_2O)(R^{f2}O)_x{-}CF_2{-}CH_2{-}OH \quad (10)$$

wherein x is an integer of from 1 to 199.

In the presence of a basic compound, to the compound (10), the compound (20) obtained in the method (13) is reacted to obtain compound (19B).

$$(CH_2{=}CHCH_2)_3C{-}CH_2OCH_2{-}(CF_2O)(R^{f2}O)_x{-}CF_2{-}CH_2OCH_2{-}C(CH_2CH{=}CH_2)_3 \quad (19B)$$

The compound (19B) and $HSiR^{23}{}_{n2}X^2{}_{3-n2}$ are subjected to a hydrosilylation reaction to obtain compound (2B).

$$[X^2{}_{3-n2}R^{23}{}_{n2}Si{-}CH_2CH_2CH_2]_3C{-}CH_2OCH_2{-}(CF_2O)(R^{f2}O)_x{-}CF_2{-}CH_2OCH_2{-}C[CH_2CH_2CH_2{-}SiR^{23}{}_{n2}X^2{}_{3-n2}]_3 \quad (2B)$$

<Method (40)>

As the starting material, commercially available compound (10) is to be used.

$$HO{-}CH_2{-}CF_2O(R^{f2}O)_x{-}CF_2{-}CH_2{-}OH \quad (10)$$

wherein x is an integer of from 1 to 199.

In accordance with the method described in J. Org. Chem., Vol. 64, 1999, p. 2564-2566, the compound (10) is oxidized to obtain compound (25).

$$HOC(O){-}(CF_2O)(R^{f2}O)_x{-}CF_2{-}C(O)OH \quad (25)$$

To the compound (25), $R^{10}OH$ is reacted to obtain compound (26).

$$R^{10}OC(O){-}(CF_2O)(R^{f2}O)_x{-}CF_2{-}C(O)OR^{10} \quad (26)$$

To the compound (26), $H_2N{-}R^{21}{-}C(CH_2CH{=}CH_2)_3$ is reacted to obtain compound (27).

$$(CH_2{=}CHCH_2)_3C{-}R^{21}{-}NHC(O){-}(CF_2O)(R^{f2}O)_x{-}CF_2{-}C(O)NH{-}R^{21}{-}C(CH_2CH{=}CH_2)_3 \quad (27)$$

The compound (27) and $HSiR^{23}{}_{n2}X^2{}_{3-n2}$ are subjected to a hydrosilylation reaction to obtain compound (2C).

$$[X^2{}_{3-n2}R^{23}{}_{n2}Si{-}CH_2CH_2CH_2]_3C{-}R^{21}{-}NHC(O){-}(CF_2O)(R^{f2}O)_x{-}CF_2{-}C(O)NH{-}R^{21}{-}C[CH_2CH_2CH_2{-}SiR^{23}{}_{n2}X^2{}_{3-n2}]_3 \quad (2C)$$

<Method (41)>

As the starting material, commercially available compound (10) is to be used.

$$HOCH_2{-}(CF_2O)(R^{f2}O)_x{-}CF_2{-}CH_2OH \quad (10)$$

wherein x is an integer of from 1 to 199.

In the presence of a basic compound, to the compound (10), the compound (30) obtained in the method (23) is reacted to obtain compound (27D).

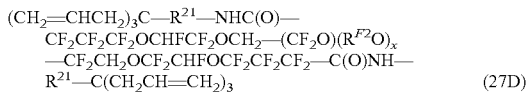
(27D)

The compound (27D) and $HSiR^{23}{}_{n2}X^{2}{}_{3-n2}$ are subjected to a hydrosilylation reaction to obtain compound (2D).

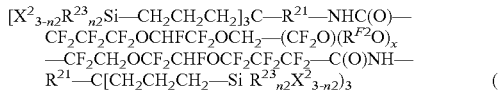
(2D)

(Compound (3))

Compound (3) is a fluorinated ether compound represented by the following formula (3).

$$A^{31}\text{-O---}(R^{f3}O)_{m3}\text{-}A^{32} \qquad (3)$$

wherein $A^{31}$ and $A^{32}$ are each independently a $C_{1-20}$ perfluoroalkyl group; $R^{f3}$ is a fluoroalkylene group having no branched structure; m3 is an integer of from 2 to 210; and $(R^{f3}O)_{m3}$ may be one composed of at least two types of $R^{f3}O$ different in number of carbon atoms.

$A^{31}$, $(R^{f3}O)_{m3}$ and $A^{32}$ may, respectively, be the same as $A^{1}$, $(R^{f1}O)_{m1}$ and $A^{1}$ in the compound (1), and their preferred examples are also the same. From such a viewpoint that a compound to be by-produced during the production of the compound (1) can be effectively utilized, they are, respectively, preferably the same as A1, $(R^{f1}O)_{m1}$ and $A^{1}$ in the compound (1).

(Preferred Form of Compound (3))

As the compound (3), from such a viewpoint that the surface layer will be further excellent in abrasion resistance and fingerprint stain removability, compound (3-1) is preferred.

$$A^{31}\text{-O-}Q^{31}\text{-}(R^{F3}O)_{m30}\text{-}[Q^{32}\text{-O}]_{p3}\text{-}A^{32} \qquad (3\text{-}1)$$

wherein $A^{31}$ and $A^{32}$ are each independently a $C_{1-20}$ perfluoroalkyl group; $Q^{31}$ is a single bond, a fluoroalkylene group containing at least one hydrogen atom and having no branched structure, a fluoroalkylene group containing at least one hydrogen atom and having no branched structure, which has an etheric oxygen atom at its terminal (but excluding the terminal on the side bonded to $A^{31}$-O), a fluoroalkylene group with at least two carbon atoms containing at least one hydrogen atom and having no branched structure, which has an etheric oxygen atom between its carbon-carbon atoms, or a fluoroalkylene group with at least two carbon atoms containing at least one hydrogen atom and having no branched structure, which has an etheric oxygen atom between its carbon-carbon atoms and at its terminal (but excluding the terminal on the side bonded to $A^{31}$-O) (provided that the number of oxygen atoms is at most 10); $Q^{32}$ is a fluoroalkylene group containing at least one hydrogen atom and having no branched structure, or a fluoroalkylene group with at least two carbon atoms containing at least one hydrogen atom and having no branched structure, which has an etheric oxygen atom between its carbon-carbon atoms (provided that the number of oxygen atoms is at most 10); $R^{F3}$ is a perfluoroalkylene group having no branched structure; m30 is an integer of from 2 to 200; $(R^{F3}O)_{m30}$ may be one composed of at least two types of $R^{F3}O$ different in number of carbon atoms; p3 is 0 when $Q^{31}$ is a single bond, and 1 when $Q^{31}$ is other than a single bond.

$A^{31}$, $Q^{31}$, $(R^{F3}O)_{m30}$, $Q^{32}$ and $A^{32}$ may, respectively, be the same as $A^{1}$, $Q^{11}$, $(R^{F1}O)_{m10}$, $Q^{11}$ (but excluding a single bond) and $A^{1}$ in the compound (1-1), and their preferred examples are also the same. From such a viewpoint that a compound to be by-produced during the production of the compound (1-1) can be effectively utilized, they are preferably the same as $A^{1}$, $Q^{11}$, $(R^{F1}O)_{m10}$, $Q^{11}$ (but excluding a single bond) and $A^{1}$ in the compound (1-1).

In a case where $Q^{31}$ is a fluoroalkylene group containing at least one hydrogen atom and having no branched structure, or a fluoroalkylene group with at least two carbon atoms containing at least one hydrogen atom and having no branched structure, which has an etheric oxygen atom between its carbon-carbon atoms, and no etheric oxygen atom is present at the terminal of $Q^{31}$ on the side bonded to $(R^{F3}O)_{m30}$, at least one hydrogen atom is bonded to the carbon atom at the terminal of $Q^{31}$ on the side bonded to $(R^{F3}O)_{m30}$.

(Method for Producing Compound (3))

As the method for producing the compound (3), for example, the following methods (50) and (51) may be mentioned.

<Method (50)>

The compound (3A) is isolated from a mixture of the compound (11), the compound (3A) and unreacted compound (10) obtained in the method (10).

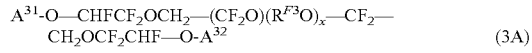
(3A)

<Method (51)>

The compound (3A) is fluorinated by fluorine gas to obtain compound (3B).

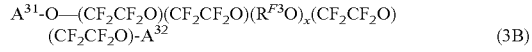
(3B)

As the compound (3) wherein $Q^{31}$ is a single bond and p3 is 0, a commercially available product may be used. As the commercially available product, FOMBLIN (registered trademark) M, FOMBLIN (registered trademark) Y, FOMBLIN (registered trademark) Z (manufactured by Solvay Solexis), Krytox (registered trademark) (manufactured by DuPont), Demnum (registered trademark) (manufactured by Daikin Industries, Ltd.), etc. may be mentioned.

The compound (4) is a compound wherein in the compound (1), $-C[-R^{12}-SiR^{13}{}_{n1}X^{1}{}_{3-n1}]_3$ is substituted by $-C[-R^{12}-SiR^{13}{}_{n1}X^{1}{}_{3-n1}]_{3-t}[R^{15}]_t$, and it is the same compound as the compound (1) except for the portion $-C[-R^{12}-SiR^{13}{}_{n1}X^{1}{}_{3-n1}]_{3-t}[-R^{15}]_t$. $R^{15}$ is a group which becomes $[-R^{12}-SiR^{13}{}_{n1}X^{1}{}_{3-n1}]$ by a hydrosilylation reaction, or its isomer group, and t is an integer of from 1 to 3.

As described above, $[-R^{12}-SiR^{13}{}_{n1}X^{1}{}_{3-n1}]$ is formed by a hydrosilylation reaction wherein $HSiR^{13}{}_{n1}X^{1}{}_{3-n1}$ is added to an alkenyl moiety having an unsaturated group at the terminal. For example, by adding $HSiR^{13}{}_{n1}X^{1}{}_{3-n1}$ to $-C(CH_2CH=CH_2)_3$, $-C[-CH_2CH_2CH_2-SiR^{13}{}_{n1}X^{1}{}_{3-n1}]_3$ will be formed. In this case, $(CH_2CH=CH_2)$ is $R^{15}$. In the hydrosilylation reaction, there may be a case where a side reaction takes place to form an alkenyl group so-called an inner olefin, wherein a terminal unsaturated group of $R^{15}$ is isomerized to a non-terminal position. For example, $-CH_2CH=CH_2$ may be isomerized to $-CH=CHCH_3$. The alkenyl group portion having an unsaturated group at a non-terminal position will remain without reacting with $HSiR^{13}{}_{n1}X^{1}{}_{3-n1}$.

In the hydrosilylation reaction in the production of the compound (1), when $R^{15}$ remains as unreacted, or when $R^{15}$ is isomerized, a compound will be by-produced wherein its terminal is —C[—R$^{12}$—SiR$^{13}_{n1}$X$^1_{3-n1}$]$_{3-t}$[—R$^{15}$]$_t$, and this compound is compound (4).

(Composition of the Present Composition)

The total proportion of the present compound and other fluorinated ether compound in the present composition is preferably 80 to 100 mass %, particularly preferably 85 to 100 mass %. That is, the proportion of impurities is preferably at most 20 mass %, particularly preferably at most 15 mass %. When the proportion of the present compound and other fluorinated ether compound is within the above range, the surface layer will be excellent in water/oil repellency, abrasion resistance, fingerprint stain removability, lubricity and outer appearance.

The proportion of other fluorinated ether compound to the total of the present compound and other fluorinated ether compound is preferably more than 0 mass % and less than 40 mass %, more preferably more than 0 mass % and at most 30 mass %, particularly preferably more than 0 mass % and at most 20 mass %. That is, the proportion of the present compound is preferably more than 60 mass % and less than 100 mass %, more preferably at least 70 mass % and less than 100 mass %, particularly preferably at least 80 mass % and less than 100 mass %. When the proportions of the present compound and other fluorinated ether compound are within the above ranges, the surface layer will be excellent in water/oil repellency, abrasion resistance, fingerprint stain removability, lubricity and outer appearance.

Here, in a case where at least one member selected from the compound (2), the compound (3) and the compound (4) is contained as said other fluorinated ether compound, the composition of the present composition will be as follows.

In the present ether composition, the total proportion of the present compound, the compound (2), the compound (3) and the compound (4) is preferably more than 60 mass % and at most 100 mass %, more preferably from 70 to 100 mass %, particularly preferably from 80 to 100 mass %. That is, the total proportion of impurities and fluorinated ether compounds other than the present compound, the compound (2), the compound (3) and the compound (4) is preferably less than 40 mass %, more preferably at most 30 mass %, particularly preferably at most 20 mass %.

The proportion of the compound (2) to the total of the present compound, the compound (2), the compound (3) and the compound (4), is preferably more than 0 mass % and less than 40 mass %, more preferably from 0 to 30 mass %, particularly preferably from 0 to 20 mass %. The proportions of the compound (3) and the compound (4) are also similar to the proportion of the compound (2).

However, the total proportion of the compound (2), the compound (3) and the compound (4), to the total of the present compound, the compound (2), the compound (3) and the compound (4), is preferably more than 0 mass % and less than 40 mass %, particularly preferably more than 0 mass % and at most 30 mass %.

In a case where at least one member selected from the compound (2), the compound (3) and the compound (4) is contained as other fluorinated ether compound, when the composition of the present composition is within the above range, the surface layer will be excellent in water/oil repellency, abrasion resistance, fingerprint stain removability, lubricity and outer appearance.

The present compositions may contain impurities other than the present compound and other fluorinated ether compound. As impurities other than the present compound and other fluorinated ether compound, unavoidable compounds, etc. in the production of the present compound and other fluorinated ether compound, may be mentioned. The present composition does not contain a liquid state liquid medium which will be described later.

[Coating Liquid]

The coating liquid of the present invention (hereinafter referred to also as the present coating liquid) comprises the present compound or present composition and a liquid medium. The coating liquid may be any liquid and may be a solution or a dispersion.

The present coating liquid may be one which contains the present compound or the present composition and may contain impurities such as by-products, etc. formed in the process for producing the present compound.

The concentration of the present compound or the present composition is preferably from 0.001 to 10 mass %, particularly preferably from 0.1 to 1 mass %, in the coating liquid.

The liquid medium is preferably an organic solvent. The organic solvent may be fluorinated organic solvent or a non-fluorinated organic solvent, or may contain both solvents.

The fluorinated organic solvent may, for example, be a fluorinated alkane, a fluorinated aromatic compound, a fluoroalkyl ether, a fluorinated alkylamine, a fluoroalcohol, etc.

As the fluorinated alkane, a compound having from 4 to 8 carbon atoms is preferred. Commercially available products may, for example, be $C_6F_{13}H$ (manufactured by Asahi Glass Company, Limited, ASAHIKLIN (registered trademark) AC-2000), $C_6F_{13}C_2H_5$ (manufactured by Asahi Glass Company, Limited, ASAHIKLIN (registered trademark) AC-6000), $C_2F_5CHFCHFCF_3$ (manufactured by Chemours, Vertrel (registered trademark) XF), etc.

As the fluorinated aromatic compound, for example, hexafluorobenzene, trifluoromethylbenzene, perfluorotoluene, bis(trifluoromethyl)benzene, etc. may be mentioned.

As the fluoroalkyl ether, a compound having from 4 to 12 carbon atoms is preferred. Commercially available products may, for example, be $CF_3CH_2OCF_2CF_2H$ (manufactured by Asahi Glass Company, Limited, ASAHIKLIN (registered trademark) AE-3000), $C_4F_9OCH_3$ (manufactured by 3M, Novec (registered trademark) 7100), $C_4F_9OC_2H_5$ (manufactured by 3M, Novec (registered trademark) 7200), $C_2F_5CF(OCH_3)C_3F_7$ (manufactured by 3M, Novec (registered trademark) 7300), etc.

As the fluorinated alkyl amine, for example, perfluorotripropylamine, perfluorotributylamine, etc. may be mentioned.

As the fluoroalcohol, for example, 2,2,3,3-tetrafluoropropanol, 2,2,2-trifluoroethanol, hexafluoroisopropanol, etc. may be mentioned.

As the non-fluorinated organic solvent, a compound consisting of only hydrogen and carbon atoms, or a compound consisting of only hydrogen, carbon and oxygen atoms, is preferred, and a hydrocarbon-type organic solvent, an alcohol-type organic solvent, a ketone-type organic solvent, an ether-type organic solvent or an ester-type organic solvent may be mentioned.

The present coating liquid contains the liquid medium in an amount of preferably from 90 to 99.999 mass %, particularly preferably from 99 to 99.9 mass %.

The present coating liquid may contain, in addition to the present compound and the liquid medium, other components in a range not to impair the effects of the present invention.

Other components may, for example, be known additives such as acid catalysts or basic catalysts for promoting hydrolysis and condensation reaction of hydrolyzable silyl groups.

In the present coating liquid, the proportion of such other components is preferably at most 10 mass %, particularly preferably at most 1 mass %.

The solid content concentration in the present coating liquid is preferably from 0.001 to 10 mass %, particularly preferably from 0.01 to 1 mass %. The solid content concentration in the coating liquid is a value calculated from the mass of the coating liquid before heating and the mass after heating for 4 hours at 120° C. in a convection dryer. The concentration of the present composition can be calculated from the solid content concentration, and the charged amounts of the present composition and the solvent, etc.

[Article]

The article of the present invention has a surface layer formed of the present compound or the present composition at the surface of a substrate.

(Surface Layer)

In the present compound or the present composition, silanol groups (Si—OH) are formed by a hydrolysis reaction of hydrolyzable silyl groups ($SiR^{13}_{n1}X^{1}_{3-n1}$) in the present compound, and such silanol groups are intermolecularly reacted to form Si—O—Si bonds, or such silanol groups undergo a dehydration condensation reaction with hydroxy groups (substrate-OH) on the surface of a substrate to form chemical bonds (substrate-O—Si). That is, the surface layer in the present invention contains the present compound in such a state that part or all of hydrolyzable silyl groups in the present compound underwent a hydrolysis reaction.

The thickness of the surface layer is preferably from 1 to 100 nm, particularly preferably from 1 to 50 nm. When the thickness of the surface layer is at least the lower limit in the above range, the effect by surface treatment tends to be sufficiently obtained. When the thickness of the surface layer is at most the upper limit value in the above range, utilization efficiency will be high. The thickness of the surface layer can be calculated from the oscillation period of an interference pattern of reflected X-ray by obtaining the interference pattern of the reflected X-ray by means of an X-ray diffractometer for thin film analysis (manufactured by Rigaku Corporation, ATX-G).

(Substrate)

The substrate in the present invention is not particularly limited as long as it is a substrate which is required to have water/oil repellency imparted. The material for the substrate may, for example, be a metal, a resin, glass, sapphire, ceramic, stone, or a composite material thereof. The glass may have been chemically strengthened. The substrate may have its surface treated with e.g. $SiO_2$.

As the substrate, a substrate for a touch panel, or a substrate for display, is preferred, and a substrate for a touch panel is particularly preferred. The substrate for a touch panel has a light-transmitting property. "Having a light-transmitting property" means that the vertical incidence type visible light transmittance in accordance with JIS R 3106: 1998 (ISO 9050: 1990) is at least 25%. As the material for the touch panel substrate, glass or a transparent resin is preferred.

(Method of Producing Article)

The article of the present invention may be produced, for example, by the following methods.

A method of treating the surface of a substrate by a dry coating method using the present compound or the present composition, to obtain an article of the present invention.

A method of applying the present coating liquid to the surface of a substrate by a wet coating method, followed by drying to obtain an article of the present invention.

<Dry Coating Method>

The present compound and the present compositions can be used as they are in a dry coating method. The present compound and the present composition are suitable for forming a surface layer excellent in adhesion by a dry coating method. As the dry coating method, a method of e.g. vacuum deposition, CVD or sputtering may be mentioned. From the viewpoint of suppressing the decomposition of the present compound and from the viewpoint of simplicity of apparatus, a vacuum deposition method can be suitably used.

<Wet Coating Method>

As the wet coating method, a spin coating method, a wipe coating method, a spray coating method, a squeegee coating method, a dip coating method, a die coating method, an ink-jet method, a flow coating method, a roll coating method, a casting method, a Langmuir-Blodgett method, a gravure coating method, etc. may be mentioned.

<Post-Treatment>

In order to improve the abrasion resistance of the surface layer, as the case requires, an operation to promote the reaction between the present compound and the substrate may be carried out. As such an operation, heating, humidification, light irradiation, etc. may be mentioned. For example, by heating the substrate having a surface layer formed, in an atmosphere having moisture, it is possible to accelerate a reaction such as a hydrolysis reaction of hydrolyzable silyl groups to silanol groups, a reaction of silanol groups with hydroxy groups at the surface of the substrate, or a condensation reaction of silanol groups to form siloxane bonds.

After the surface treatment, among compounds in the surface layer, other compounds or compounds not chemically bonded to the substrate may be removed as the case requires. As a specific method, for example, a method of letting a solvent flow on the surface layer, or a method of wiping the surface layer with a cloth soaked with a solvent, may be mentioned.

EXAMPLES

Now, the present invention will be described in further detail with reference to Examples, but the present invention is not limited to these Examples.

Hereinafter, "%" is "mass %" unless otherwise specified. Further, a mixture made of at least two types of compound (1) will be referred to as a "compound" and one made of compound (1) and other fluorinated ether compound will be referred to as a "composition".

Ex. 1 to 6, 11 to 16, 17 to 22, 27 to 36, 38 to 41, 43 to 45 and 48 to 53 are Examples of the present invention, and Ex. 7 to 10, 23 to 26, 37, 42, 46 and 47 are Comparative Examples.

Ex. 1: Production of Compound (1A-1) and Compound (3A-1)

Ex. 1-1

Into a 300 mL three-necked flask, 24.4 g of a 24% KOH aqueous solution, 33 g of tert-butyl alcohol, 220 g of compound (10-1) (manufactured by Solvay Solexis, FLUOROLINK (registered trademark) D4000) were put, and 19.4 g of $CF_3CF_2CF_2O—CF=CF_2$ (manufactured by Tokyo Chemical Industry Co., Ltd.) was added. Under a nitrogen atmosphere, the mixture was stirred at 60° C. for 8 hours. After washing it once with dilute aqueous hydrochloric acid, the organic phase was collected and concentrated by an evaporator to obtain 233 g of crude product (a). The crude product (a) was fractionated by developing it by silica gel column chromatography. As the developing solvents, $C_6F_{13}CH_2CH_3$ (manufactured by Asahi Glass Company, Limited, AC-6000), AC-6000/$CF_3CH_2OCF_2CF_2H$ (manufactured by Asahi Glass Company, Limited, AE-3000)=1/2 (mass ratio) and AE-3000/ethyl acetate=9/1 (mass ratio) were used in this order. With respect to each fraction, the structures of terminal groups and the mean values of unit numbers (x1, x2) of structural units were obtained from the integral values of $^1$H-NMR and $^{19}$F-NMR. It was found that in the crude product (a), compound (11-1), compound (3A-1) and compound (10-1) were contained in amounts of 42 mol %, 49 mol % and 9 mol %, respectively. 98.6 g (yield: 44.8%) of compound (11-1) and 51.9 g (yield: 23.6%) of compound (3A-1) were obtained.

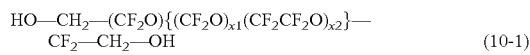
$$HO—CH_2—(CF_2O)\{(CF_2O)_{x1}(CF_2CF_2O)_{x2}\}—CF_2—CH_2—OH \qquad (10\text{-}1)$$

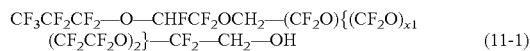
$$CF_3CF_2CF_2—O—CHFCF_2OCH_2—(CF_2O)\{(CF_2O)_{x1}(CF_2CF_2O)_{x2}\}—CF_2—CH_2—OH \qquad (11\text{-}1)$$

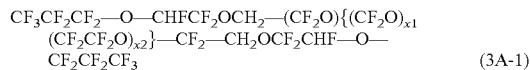
$$CF_3CF_2CF_2—O—CHFCF_2OCH_2—(CF_2O)\{(CF_2O)_{x1}(CF_2CF_2O)_{x2}\}—CF_2—CH_2OCF_2CHF—O—CF_2CF_2CF_3 \qquad (3A\text{-}1)$$

NMR spectrum of compound (11-1);
$^1$H-NMR (300.4 MHz, solvent: $CDCl_3$, reference: TMS) δ (ppm): 3.9 (2H), 4.2 (2H), 5.8 to 6.0 (1H).
$^{19}$F-NMR (282.7 MHz, solvent: $CDCl_3$, reference: $CFCl_3$) δ (ppm): −52.4 to −55.8 (42F), −78.8 (1F), −80.8 (1F), −81.4 (1F), −82.2 (3F), −83.5 (1F), −85.3 to −88.2 (2F), −89.4 to −91.1 (82F), −130.5 (2F), −145.1 (1F).
Mean value of the unit number x1: 21, mean value of the unit number x2: 20, number average molecular weight of compound (11-1): 4,150.

NMR spectrum of compound (3A-1);
$^1$H-NMR (300.4 MHz, solvent: $CDCl_3$, reference: TMS) δ (ppm): 4.2 (4H), 5.8 to 6.0 (2H).
$^{19}$F-NMR (282.7 MHz, solvent: $CDCl_3$, reference: $CFCl_3$) δ (ppm): −52.4 to −55.8 (42F), −78.8 (2F), −80.7 (2F), −82.2 (6F), −85.3 to −88.2 (4F), −89.4 to −91.1 (84F), −130.5 (4F), −145.1 (2F).
Mean value of the unit number x1: 21, mean value of the unit number x2: 20, number average molecular weight of compound (3A-1): 4,420.

Ex. 1-2

Into a 100 mL eggplant flask, 30.0 g of compound (11-1), 0.9 g of sodium fluoride powder and 30 g of dichloropentafluoropropane (manufactured by Asahi Glass Company, Limited, AK-225) were put, and 3.5 g of $CF_3CF_2CF_2OCF(CF_3)C(O)F$ was added. Under a nitrogen atmosphere, the mixture was stirred at 50° C. for 24 hours. After removal of sodium fluoride powder by a pressure filter, excess $CF_3CF_2CF_2OCF(CF_3)C(O)F$ and AK-225 were distilled off under reduced pressure. The obtained crude product was diluted with $C_6F_{13}H$ (manufactured by Asahi Glass Company, Limited, AC-2000), and passed through a silica gel column, whereupon the recovered solution was concentrated by an evaporator, to obtain 31.8 g (yield: 98.8%) of compound (12-1).

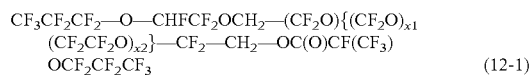
$$CF_3CF_2CF_2—O—CHFCF_2OCH_2—(CF_2O)\{(CF_2O)_{x1}(CF_2CF_2O)_{x2}\}—CF_2—CH_2—OC(O)CF(CF_3)OCF_2CF_2CF_3 \qquad (12\text{-}1)$$

NMR spectrum of compound (12-1);
$^1$H-NMR (300.4 MHz, solvent: $CDCl_3$, reference: TMS) δ (ppm): 4.2 (2H), 4.7 (2H), 5.8 to 6.0 (1H).
$^{19}$F-NMR (282.7 MHz, solvent: $CDCl_3$, reference: $CFCl_3$) δ (ppm): −52.4 to −55.8 (42F), −78.8 to −88.2 (17F), −89.4 to −91.1 (82F), −130.3 (2F), −130.5 (2F), −132.5 (1F), −145.1 (1F).
Mean value of the unit number x1: 21, mean value of the unit number x2: 20, number average molecular weight of compound (12-1): 4,460.

Ex. 1-3

At a gas outlet of a 1 L nickel autoclave, a cooler maintained at 20° C., a NaF pellet packed layer and a cooler maintained at 0° C. were installed in series. A liquid returning line to return a liquid collected from the cooler maintained at 0° C. to the autoclave, was installed.

Into the autoclave, 750 g of $ClCF_2CFClCF_2OCF_2CF_2Cl$ (hereinafter referred to also as CFE-419) was put and stirred while maintaining the temperature at 25° C. After blowing nitrogen gas into the autoclave at 25° C. for 1 hour, 20% fluorine gas was blown at 25° C. for one hour at a flow rate of 2.0 L/hour. While blowing 20% fluorine gas at the same flow rate, a solution prepared by dissolving 31.0 g of compound (12-1) in 124 g of CFE-419 was injected into the autoclave over a period of 4.3 hours. While blowing 20% fluorine gas at the same flow rate, the internal pressure of the autoclave was raised to 0.15 MPa (gauge pressure). Into the autoclave, 4 mL of a benzene solution containing 0.05 g/mL of benzene in CFE-419, was injected while heating to 40° C. from 25° C., and then the benzene solution inlet of the autoclave was closed. After stirring for 15 minutes, 4 mL of the benzene solution was injected again while maintaining the temperature at 40° C., and then the inlet was closed. The same operation was repeated three more times. The total amount of benzene injected was 0.17 g. While blowing 20% fluorine gas at the same flow rate, stirring was continued for 1 hour. The pressure in the autoclave was set at atmospheric pressure, and nitrogen gas was blown in for 1 hour. The content of the autoclave was concentrated by an evaporator to obtain 31.1 g (yield: 98.5%) of compound (13-1).

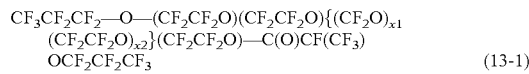
$$CF_3CF_2CF_2—O—(CF_2CF_2O)(CF_2CF_2O)\{(CF_2O)_{x1}(CF_2CF_2O)_{x2}\}(CF_2CF_2O)—C(O)CF(CF_3)OCF_2CF_2CF_3 \qquad (13\text{-}1)$$

NMR spectrum of compound (13-1);
$^{19}$F-NMR (282.7 MHz, solvent: $CDCl_3$, reference: $CFCl_3$) δ (ppm): −52.4 to −55.7 (42F), −78.8 to −88.1 (11F), −89.4 to −91.1 (92F), −91.5 (2F), −130.3 (2F), −130.5 (2F), −132.5 (1F).
Mean value of the unit number x1: 21, mean value of the unit number x2: 20, number average molecular weight of compound (13-1): 4,550.

Ex. 1-4

Into a round bottom flask made of a tetrafluoroethylene-perfluoro(alkoxy vinyl ether) copolymer (hereinafter referred to also as PFA), 30.0 g of compound (13-1) and 60 g of AK-225 were put. The mixture was stirred while cooling in an ice bath, and under a nitrogen atmosphere, 2.0 g of methanol was dropwise slowly added from a dropping funnel. While bubbling with nitrogen, the mixture was stirred for 12 hours. The reaction mixture was concentrated by an evaporator to obtain 27.6 g (yield: 98.8%) of compound (14-1).

(14-1)

NMR spectrum of compound (14-1);
$^1$H-NMR (300.4 MHz, solvent: CDCl$_3$, reference: TMS) δ (ppm): 3.9 (3H).
$^{19}$F-NMR (282.7 MHz, solvent: CDCl$_3$, reference: CFCl$_3$) δ (ppm): −52.4 to −55.8 (42F), −82.2 (3F), −89.4 to −91.1 (92F), −30.5 (2F).

Mean value of the unit number x1: 21, mean value of the unit number x2: 20, number average molecular weight of the compound (14-1): 4,230.

Ex. 1-5

In a 100 mL three-necked eggplant flask, 0.18 g of lithium chloride was dissolved in 18.3 g of ethanol. 25.0 g of the compound (14-1) was added thereto, and while cooling in an ice bath, a solution prepared by dissolving 0.75 g of sodium borohydride in 22.5 g of ethanol, was dropwise slowly added. The ice bath was removed, and stirring was continued while slowly warming to room temperature. After stirring for 12 hours at room temperature, aqueous hydrochloric acid was dropwise added until the liquid became acidic. 20 mL of AC-2000 was added, followed by washing once with water and once with saturated brine, whereupon the organic phase was collected. The collected organic phase was concentrated by an evaporator to obtain 24.6 g (yield: 99.0%) of compound (15-1).

(15-1).

NMR spectrum of compound (15-1);
$^1$H-NMR (300.4 MHz, solvent: CDCl$_3$, reference: TMS) δ (ppm): 3.9 (2H).
$^{19}$F-NMR (282.7 MHz, solvent: CDCl$_3$, reference: CFCl$_3$) δ (ppm): −52.4 to −55.7 (42F), −81.4 (1F), −82.2 (3F), −83.4 (1F), −89.4 to −91.1 (90F), −130.5 (2F).

Mean value of the unit number x1: 21, mean value of the unit number x2: 20, number average molecular weight of the compound (15-1): 4,200.

Ex. 1-6

Into a 100 mL two-necked eggplant flask, 20.0 g of the compound (15-1), 20.0 g of 1,3-bis(trifluoromethyl)benzene (manufactured by Tokyo Chemical Industry Co., Ltd.), 1.01 g of CF$_3$SO$_2$Cl (manufactured by Wako Pure Chemical Industries, Ltd.) and 1.00 g of triethylamine were put, and stirred at room temperature for 4 hours under a nitrogen atmosphere. After completion of the reaction, 15 g of AK-225 was added, followed by washing once with each of water and saturated brine, whereupon the organic phase was collected. The collected organic phases was concentrated by an evaporator to obtain 20.3 g (yield: 99%) of compound (16-1).

(16-1)

NMR spectrum of compound (16-1);
$^1$H-NMR (300.4 MHz, solvent: CDCl$_3$, reference: TMS) δ (ppm): 4.6 (2H).
$^{19}$F-NMR (282.7 MHz, solvent: CDCl$_3$, reference: CFCl$_3$) δ (ppm): −52.4 to −55.7 (42F), −74.1 (3F), −76.1 (1F), −79.5 (1F), −82.2 (3F), −89.4 to −91.1 (90F), −130.5 (2F).

Mean value of the unit number x1: 21, mean value of the unit number x2: 20, number average molecular weight of the compound (16-1): 4,340.

Ex. 1-7

In an 50 mL eggplant flask, 0.13 g of sodium hydride (55%/paraffin) was suspended in 5.0 g of 1,3-bis(trifluoromethyl)benzene (manufactured by Tokyo Chemical Industry Co., Ltd.), and 10.0 g of the compound (16-1) was dropwise added at room temperature. To this, 0.91 g of HOCH$_2$C (CH$_2$OCH$_2$CH=CH$_2$)$_3$ (manufactured by DAISO CO., LTD. purified product of NEOALLYL (registered trademark) P-30M) was added, followed by heating to 70° C. and stirring for 12 hours. After completion of the reaction, 15 g of AK-225 was added, followed by washing with water, whereupon the organic phase was collected and concentrated by an evaporator. This was purified by silica gel column chromatography (developing solvent: AE-3000/ethyl acetate=99/1 (mass ratio)) to obtain 2.6 g (yield: 26%) of compound of (17-1).

(17-1)

NMR spectrum of compound (17-1);
$^1$H-NMR (300.4 MHz, solvent: CDCl$_3$, reference: TMS) δ (ppm): 3.6 (6H), 3.7 to 3.9 (10H), 5.1 (6H), 5.8 (3H).
$^{19}$F-NMR (282.7 MHz, solvent: CDCl$_3$, reference: CFCl$_3$) δ (ppm): −52.4 to −55.7 (42F), −77.2 (1F), −79.4 (1F), −82.2 (3F), −89.4 to −91.1 (90F), −130.5 (2F).

Mean value of the unit number x1: 21, mean value of the unit number x2: 20, number average molecular weight of the compound (17-1): 4,450.

Ex. 1-8

Into a 10 mL container made of PFA, 2.0 g of the compound (17-1), 0.002 g of a xylene solution (platinum content: 2%) of a platinum/1,3-divinyl-1,1,3,3-tetramethyl-disiloxane complex, 0.24 g of HSi(OCH$_3$)$_3$, 0.003 g of dimethyl sulfoxide and 0.15 g of 1,3-bis(trifluoromethyl) benzene (manufactured by Tokyo Chemical Industry Co., Ltd.) were put and stirred at 40° C. for 4 hours. After completion of the reaction, the solvent, etc. were distilled off under reduced pressure, followed by filtration through a membrane filter having a pore size of 0.2 μm, to obtain 1.9 g (yield 92%) of a composition (1) comprising compound (1A-1) wherein three allyl groups of the compound (17-1) were hydrosilylated and a by-product wherein some or all of three allyl groups of the compound (17-1) were isomerized to an inner olefin (—CH=CHCH$_3$). The conversion in the hydrosilylation was 100%, and no compound (17-1) remained. The selectivity in the hydrosilylation was 85%.

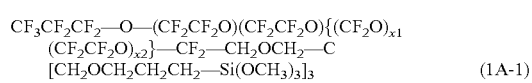
(1A-1)

NMR spectrum of compound (1A-1);
$^1$H-NMR (300.4 MHz, solvent: CDCl$_3$, reference: TMS) δ (ppm): 0.7 (6H), 1.7 (6H), 3.4-3.8 (44H).
$^{19}$F-NMR (282.7 MHz, solvent: CDCl$_3$, reference: CFCl$_3$) δ (ppm): −52.4 to −55.7 (42F), −77.2 (1F), −79.4 (1F), −82.2 (3F), −89.4 to −91.1 (90F), −130.5 (2F).

Mean value of the unit number x1: 21, mean value of the unit number x2: 20, number average molecular weight of the compound (1A-1): 4,810.

Ex. 2: Production of Compound (1B-1)

Ex. 2-1

30.6 g (yield: 99%) of compound (16B-1) was obtained in the same manner as in Ex. 1-6 except that the compound (15-1) was changed to 30.0 g of the compound (11-1) obtained in Ex. 1-1, the amount of 1,3-bis(trifluoromethyl)benzene (manufactured by Tokyo Chemical Industry Co., Ltd.) was changed to 30.0 g, the amount of $CF_3SO_2Cl$ (manufactured by Wako Pure Chemical Industries, Ltd.) was changed to 1.44 g, and the amount of triethylamine was changed to 1.45 g.

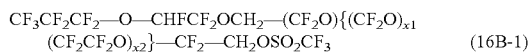

(16B-1)

NMR spectrum of compound (16B-1);
$^1$H-NMR (300.4 MHz, solvent: $CDCl_3$, reference: TMS) δ (ppm): 4.2 (2H), 4.6 (2H), 5.8 to 6.0 (1H).
$^{19}$F-NMR (282.7 MHz, solvent: $CDCl_3$, reference: $C_6F_6$) δ (ppm): −51.2 to −54.6 (42F), −74.1 (3F), −77.6 (1F), −77.6 (2F), −79.0 (1F), −79.5 (1F), −81.2 (3F), −84.3 to −87.2 (2F), −87.9 to −91.0 (82F), −129.4 (2F), 144.1 (1F).

Mean value of the unit number x1: 21, mean value of the unit number x2: 20, number average molecular weight of the compound (16B-1): 4,280.

Ex. 2-2

2.4 g (yield: 24%) of compound (17B-1) was obtained in the same manner as in Ex. 1-7, except that the compound (16-1) was changed to the compound (16B-1), the amount of $HOCH_2C(CH_2OCH_2CH=CH_2)_3$ was changed to 0.92 g.

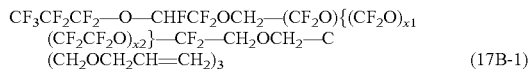

(17B-1)

NMR spectrum of compound (17B-1);
$^1$H-NMR (300.4 MHz, solvent: $CDCl_3$, reference: TMS) δ (ppm): 3.6 (6H), 3.7 to 3.9 (10H), 4.2 (2H), 5.1 (6H), 5.7 to 6.0 (4H).
$^{19}$F-NMR (282.7 MHz, solvent: $CDCl_3$, reference: $C_6F_6$) δ (ppm): −51.2 to −54.6 (42F), −77.2 (1F), −77.7 (1F), −79.3 (1F), −79.7 (1F), −81.2 (3F), −84.3 to −87.2 (2F), −87.9 to −91.0 (82F), −129.4 (2F), −144.1 (1F).

Mean value of the unit number x1: 21, mean value of the unit number x2: 20, number average molecular weight of the compound (17B-1): 4,390.

Ex. 2-3

In the same manner as in Ex. 1-8, except that the compound (17-1) was changed to 1.8 g of the compound (17B-1) obtained in Ex. 2-2 and the amount of $HSi(OCH_3)_3$ was changed to 0.22 g, 1.7 g (yield 87%) of a composition (2) comprising compound (1B-1) wherein three allyl groups in the compound (17B-1) were hydrosilylated and a by-product wherein some or all of three allyl groups in the compound (17B-1) were isomerized to an inner olefin (—CH=CHCH$_3$), was obtained. The conversion in the hydrosilylation was 100%, and no compound (17B-1) remained. The selectivity in the hydrosilylation was 87%.

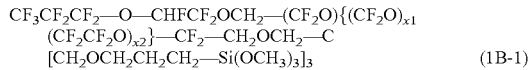

(1B-1)

NMR spectrum of compound (1B-1);
$^1$H-NMR (300.4 MHz, solvent: $CDCl_3$, reference: TMS) δ (ppm): 0.7 (6H), 1.7 (6H), 3.4-3.8 (44H), 4.2 (2H), 5.8 to 6.0 (1H).
$^{19}$F-NMR (282.7 MHz, solvent: $CDCl_3$, reference: $C_6F_6$) δ (ppm): −51.2 to −54.6 (42F), −77.2 (1F), −77.7 (1F), −79.3 (1F), −79.7 (1F), −81.2 (3F), −84.3 to −87.2 (2F), −87.9 to −91.0 (82F), −129.4 (2F), −144.1 (1F).

Mean value of the unit number x1: 21, mean value of the unit number x2: 20, number average molecular weight of the compound (1B-1): 4,760.

Ex. 3: Production of Compound (1C-1)

Ex. 3-1

Compound (15C-1) was obtained in accordance with the method described in Example 7 in WO2013/121984.

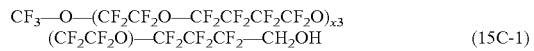

(15C-1)

NMR spectrum of compound (15C-1);
$^1$H-NMR (300.4 MHz, solvent: $CDCl_3$, reference: TMS) δ (ppm): 2.0 (1H), 4.0 (2H).
$^{19}$F-NMR (282.7 MHz, solvent: $CDCl_3$, reference: $CFCl_3$) δ (ppm): −56.2 (3F), −84.1 (54F), −89.3 (54F), −91.4 (2F), −123.7 (2F), −126.6 (52F), −128.7 (2F).

Mean value of the unit number x3: 13, number average molecular weight of the compound (15C-1): 4,700.

Ex. 3-2

30.6 g (yield: 99%) of compound (16C-1) was obtained in the same manner as in Ex. 1-6 except that the compound (15-1) was changed to the compound (15C-1) obtained in Ex. 3-1, the amount of $CF_3SO_2Cl$ (manufactured by Wako Pure Chemical Industries, Ltd.) was changed to 0.86 g, and the amount of triethylamine was changed to 1.02 g.

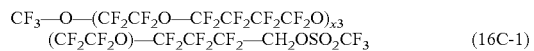

(16C-1)

NMR spectrum of compound (16C-1);
$^1$H-NMR (300.4 MHz, solvent: $CDCl_3$, reference: TMS) δ (ppm): 4.7 (2H).
$^{19}$F-NMR (282.7 MHz, solvent: $CDCl_3$, reference: $C_6F_6$) δ (ppm): −56.3 (3F), −74.0 (3F), −84.0 (54F), −89.2 (54F), −91.4 (2F), −122.7 (2F), −123.6 (2F), −26.6 (52F).

Mean value of the unit number x3: 13, number average molecular weight of the compound (16C-1): 4,830.

Ex. 3-3

3.9 g (yield: 38%) of compound (17C-1) was obtained in the same manner as in Ex. 1-7 except that the amount of sodium hydride (55%/paraffin) was changed to 0.14 g, the compound (16-1) was changed to the compound (16C-1) obtained in Ex. 3-2, the amount of $HOCH_2C(CH_2OCH_2CH=CH_2)_3$ was changed to 0.95 g, and after the completion of the reaction, no dilution with AK-225 was conducted.

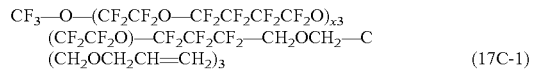

(17C-1)

NMR spectra of compound (17C-1);
$^1$H-NMR (300.4 MHz, solvent: $CDCl_3$, reference: TMS) δ (ppm): 3.6 (6H), 3.7 to 3.9 (8H), 4.0 (2H), 5.1 (6H), 5.7 to 6.0 (3H).

$^{19}$F-NMR (282.7 MHz, solvent: CDCl$_3$, reference: C$_6$F$_6$) δ (ppm): −56.3 (3F), −84.0 (54F), −89.2 (54F), −91.4 (2F), −120.5 (2F), −126.6 (52F), −128.6 (2F).

Mean value of the unit number x3: 13, number average molecular weight of the compound (17C-1): 4,940.

Ex. 3-4

In the same manner as in Ex. 1-8 except that the compound (17-1) was changed to 3.0 g of the compound (17C-1) obtained in Ex. 3-3, the amount of the platinum complex solution was changed to 0.004 g, the amount of HSi(OCH$_3$)$_3$ was changed to 0.40 g, the amount of dimethyl sulfoxide was changed to 0.006 g, the amount of 1,3-bis(trifluoromethyl)benzene (manufactured by Tokyo Chemical Industry Co., Ltd.) was changed to 0.30 g, 3.0 g (yield: 93%) of a composition (3) comprising compound (1C-1) wherein three allyl groups in the compound (170-1) are hydrosilylated and a by-product wherein part or all of three allyl groups in the compound (17C-1) were isomerized to an inner olefin (—CH=CHCH$_3$), was obtained. The conversion in the hydrosilylation was 100%, and no compound (17C-1) remained. The selectivity in the hydrosilylation was 85%.

CF$_3$—O—(CF$_2$CF$_2$O—CF$_2$CF$_2$CF$_2$CF$_2$O)$_{x3}$
(CF$_2$CF$_2$O)—CF$_2$CF$_2$CF$_2$—CH$_2$OCH$_2$—C
[CH$_2$OCH$_2$CH$_2$CH$_2$—Si(OCH$_3$)$_3$]$_3$ (1C-1)

NMR spectrum of compound (1C-1);
$^1$H-NMR (300.4 MHz, solvent: CDCl$_3$, reference: TMS) δ (ppm): 0.7 (6H), 1.7 (6H), 3.4-3.8 (44H).
$^{19}$F-NMR (282.7 MHz, solvent: CDCl$_3$, reference: C$_6$F$_6$) δ (ppm): −56.3 (3F), −84.0 (54F), −89.2 (54F), −91.4 (2F), −120.5 (2F), −126.6 (52F), −128.6 (2F).

Mean value of the unit number x3: 13, number average molecular weight of the compound (1C-1): 5,300.

Ex. 4: Production of Compound (1 D-1)

Ex. 4-1

Into a 200 mL eggplant flask, 10 g of HOCH$_2$C(CH$_2$CH=CH$_2$)$_3$, 20.0 g of 1,3-bis(trifluoromethyl)benzene (manufactured by Tokyo Chemical Industry Co., Ltd.) and 25.5 g of (CF$_3$SO$_2$)$_2$O were put, and in a nitrogen atmosphere, 19.3 g of 2,6-lutidine was dropwise added at 0° C. The mixture was heated to room temperature, followed by stirring for one hour. After completion of the reaction, washing with water was conducted, whereupon the organic phase was collected, and concentrated by an evaporator. This concentrate was purified by silica gel column chromatography (developing solvent: hexane/ethyl acetate=85/15 (mass ratio)), to obtain 15.1 g (yield: 85%) of compound (20).

CF$_3$SO$_2$OCH$_2$C(CH$_2$CH=CH$_2$)$_3$ (20)

NMR spectrum of compound (20);
$^1$H-NMR (300.4 MHz, solvent: CDCl$_3$, reference: TMS) δ (ppm): 2.1 (6H), 4.3 (2H), 5.0 to 5.2 (6H), 5.6 to 5.8 (3H).
$^{19}$F-NMR (282.7 MHz, solvent: CDCl$_3$, reference: C$_6$F$_6$) δ (ppm): −74.0 (3F).

Ex. 4-2

5.1 g (yield: 51%) of compound (17D-1) was obtained in the same manner as in Ex. 1-7, except that the compound (16-1) was changed to 0.70 g of the compound (20) obtained in Ex. 4-1, and HOCH$_2$C(CH$_2$OCH$_2$CH=CH$_2$)$_3$ was changed to 10.0 g of the compound (15-1) obtained in Ex. 1-5.

CF$_3$CF$_2$CF$_2$—O—(CF$_2$CF$_2$O)(CF$_2$CF$_2$O){(CF$_2$O)$_{x1}$
(CF$_2$CF$_2$O)$_{x2}$}—CF$_2$—CH$_2$OCH$_2$—C
(CH$_2$CH=CH$_2$)$_3$ (17D-1)

NMR spectrum of compound (17D-1);
$^1$H-NMR (300.4 MHz, solvent: CDCl$_3$, reference: TMS) δ (ppm): 2.1 (6H), 3.7 (4H), 5.0 to 5.2 (6H), 5.8 (3H).
$^{19}$F-NMR (282.7 MHz, solvent: CDCl$_3$, reference: CFCl$_3$) δ (ppm): −52.4 to −55.7 (42F), −77.2 (1F), −79.4 (1F), −82.2 (3F), −89.4 to −91.1 (90F), −130.5 (2F).

Mean value of the unit number x1: 21, mean value of the unit number x2: 20, number average molecular weight of the compound (17D-1): 4,350.

Ex. 4-3

In the same manner as in Ex. 1-8 except that the compound (17-1) was changed to the compound (17D-1) obtained in Ex. 4-2 and the amount of HSi(OCH$_3$)$_3$ was changed to 0.25 g, 1.9 g (yield: 90%) of compound (1D-1) wherein three allyl groups in the compound (17D-1) were hydrosilylated. The conversion in the hydrosilylation was 100% and no compound (17D-1) remained. The selectivity in the hydrosilylation was 100%, and no by-product was formed wherein some or all of three allyl groups in the compound (17D-1) were isomerized to an inner olefin (—CH=CHCH$_3$).

CF$_3$CF$_2$CF$_2$—O—(CF$_2$CF$_2$O)(CF$_2$CF$_2$O){(CF$_2$O)$_{x1}$
(CF$_2$CF$_2$O)$_{x2}$}—CF$_2$—CH$_2$OCH$_2$—C
[CH$_2$CH$_2$CH$_2$Si(OCH$_3$)$_3$]$_3$ (1 D-1)

NMR spectrum of compound (1 D-1);
$^1$H-NMR (300.4 MHz, solvent: CDCl$_3$, reference: TMS) δ (ppm): 0.7 (6H), 1.7 (6H), 3.4-3.8 (37H).
$^{19}$F-NMR (282.7 MHz, solvent: CDCl$_3$, reference: CFCl$_3$) δ (ppm): −52.4 to −55.7 (42F), −77.2 (1F), −79.4 (1F), −82.2 (3F), −89.4 to −91.1 (90F), −130.5 (2F).

Mean value of the unit number x1: 21, mean value of the unit number x2: 20, number average molecular weight of the compound (1 D-1): 4,710.

Ex. 5: Production of Compound (1E-1)

Ex. 5-1

5.0 g (yield: 50%) of compound (17E-1) was obtained in the same manner as in Ex. 1-7 except that the compound (16-1) was changed to 0.72 g of the compound (20) obtained in Ex. 4-1, HOCH$_2$C(CH$_2$OCH$_2$CH=CH$_2$)$_3$ was changed to 10.0 g of the compound (11-1) obtained in Ex. 1-1, and no dilution with AK-225 was conducted after completion of the reaction.

CF$_3$CF$_2$CF$_2$—O—CHFCF$_2$OCH$_2$—(CF$_2$O){(CF$_2$O)$_{x1}$
(CF$_2$CF$_2$O)$_{x2}$}—CF$_2$—CH$_2$OCH$_2$—C
(CH$_2$CH=CH$_2$)$_3$ (17E-1)

NMR spectrum of compound (17E-1);
$^1$H-NMR (300.4 MHz, solvent: CDCl$_3$, reference: TMS) δ (ppm): 2.1 (6H), 3.7 to 3.9 (4H), 4.2 (2H), 5.0 to 5.2 (6H), 5.7 to 6.0 (4H).
$^{19}$F-NMR (282.7 MHz, solvent: CDCl$_3$, reference: C$_6$F$_6$) δ (ppm): −51.2 to −54.6 (42F), −77.2 (1F), −77.7 (1F), −79.3 (1F), −79.7 (1F), −81.2 (3F), −84.3 to −87.2 (2F), −87.9 to −91.0 (82F), −129.4 (2F), −144.1 (1F).

Mean value of the unit number x1: 21, mean value of the unit number x2: 20, number average molecular weight of the compound (17E-1): 4,300.

Ex. 5-2

In the same manner as in Ex. 1-8 except that the compound (17-1) was changed to 1.8 g of the compound (17E-1) obtained in Ex. 5-1 and the amount of $HSi(OCH_3)_3$ was changed to 0.23 g, 1.7 g (yield: 87%) of compound (1E-1) was obtained wherein three allyl groups in the compound (17E-1) are hydrosilylated. The conversion in the hydrosilylation was 100%, and no compound (17E-1) remained. The selectivity of the hydrosilylation was 100%, and no by-product was formed wherein some or all of three allyl groups in the compound (17E-1) were isomerized to an inner olefin (—CH=CHCH$_3$).

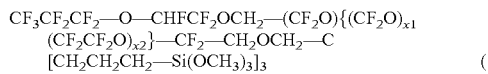
(1E-1)

NMR spectrum of compound (1E-1);
$^1$H-NMR (300.4 MHz, solvent: CDCl$_3$, reference: TMS) δ (ppm): 0.7 (6H), 1.7 (6H), 3.4-3.8 (37H), 4.2 (2H), 5.8 to 6.0 (1H).
$^{19}$F-NMR (282.7 MHz, solvent: CDCl$_3$, reference: C$_6$F$_6$) δ (ppm): −51.2 to −54.6 (42F), −77.2 (1F), −77.7 (1F), −79.3 (1F), −79.7 (1F), −81.2 (3F), −84.3 to −87.2 (2F), −87.9 to −91.0 (82F), −129.4 (2F), −144.1 (1F).

Mean value of the unit number x1: 21, mean value of the unit number x2: 20, number average molecular weight of the compound (1E-1): 4,660.

Ex. 6: Production of Compound (1F-1)

Ex. 6-1

4.9 g (yield: 48%) of compound (17F-1) was obtained in the same manner as in Ex. 1-7 except that the compound (16-1) was changed to 0.64 g of the compound (20) obtained in Ex. 4-1, HOCH$_2$C(CH$_2$OCH$_2$CH=CH$_2$)$_3$ was changed to 10.0 g of the compound (15C-1) obtained in Ex. 3-1, and no dilution with AK-225 was conducted after completion of the reaction.

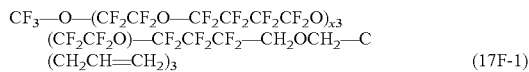
(17F-1)

NMR spectrum of compound (17F-1);
$^1$H-NMR (300.4 MHz, solvent: CDCl$_3$, reference: TMS) δ (ppm): 2.1 (6H), 3.7 to 3.9 (4H), 5.0 to 5.2 (6H), 5.7 to 6.0 (3H).
$^{19}$F-NMR (282.7 MHz, solvent: CDCl$_3$, reference: C$_6$F$_6$) δ (ppm): −56.3 (3F), −84.0 (54F), −89.2 (54F), −91.4 (2F), −120.5 (2F), −126.6 (52F), −28.6 (2F).

Mean value of the unit number x3: 13, number average molecular weight of the compound (17F−1): 4,850.

Ex. 6-2

In the same manner as in Ex. 1-8 except that the compound (17-1) was changed to the compound (17F-1) obtained in Ex. 6-1, and the amount of HSi(OCH$_3$)$_3$ was changed to 0.23 g, 1.9 g (yield: 90%) of compound (1F-1) was obtained wherein three allyl groups in the compound (17F-1) were hydrosilylated. The conversion in the hydrosilylation was 100%, and no compound (17F-1) remained. The selectivity in the hydrosilylation was 100%, and no by-product was formed wherein some or all of three allyl groups in the compound (17F-1) were isomerized to an inner olefin (—CH=CHCH$_3$).

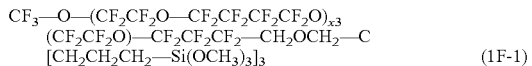
(1F-1)

NMR spectrum of compound (1F-1);
$^1$H-NMR (300.4 MHz, solvent: CDCl$_3$, reference: TMS) δ (ppm): 0.7 (6H), 1.7 (6H), 3.4-3.8 (37H).
$^{19}$F-NMR (282.7 MHz, solvent: CDCl$_3$, reference: C$_6$F$_6$) δ (ppm): −56.3 (3F), −84.0 (54F), −89.2 (54F), −91.4 (2F), −120.5 (2F), −126.6 (52F), −128.6 (2F).

Mean value of the unit number x3: 13, number average molecular weight of the compound (1F-1): 5,210.

Ex. 7: Production of Compound (2A-1)

Ex. 7-1

31.0 g (yield: 97%) of compound (18-1) was obtained in the same manner as in Ex. 1-6 except that the compound (15-1) was changed to 30.0 g of the compound (10-1), the amount of 1,3-bis(trifluoromethyl)benzene (manufactured by Tokyo Chemical Industry Co., Ltd.) was changed to 30.0 g, the amount of CF$_3$SO$_2$Cl (manufactured by Wako Pure Chemical Industries, Ltd.) was changed to 2.9 g, and the amount of triethylamine was changed to 3.0 g.

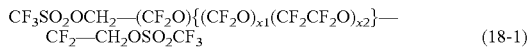
(18-1)

NMR spectrum of compound (18-1);
$^1$H-NMR (300.4 MHz, solvent: CDCl$_3$, reference: TMS) δ (ppm): 4.6 (2H).
$^{19}$F-NMR (282.7 MHz, solvent: CDCl$_3$, reference: C$_6$F$_6$) δ (ppm): −51.2 to −54.6 (42F), −74.1 (6F), −77.0 (2F), −79.0 (2F), −87.5 to −91.0 (80F).

Mean value of the unit number x1: 21, mean value of the unit number x2: 20, number average molecular weight of the compound (18-1): 4,150.

Ex. 7-2

1.5 g (yield: 14%) of compound (19-1) was obtained in the same manner as in Ex. 1-7 except that the amount of sodium hydride (55%/paraffin) was changed to 0.25 g, the amount of 1,3-bis(trifluoromethyl)benzene (manufactured by Tokyo Chemical Industry Co., Ltd.) was changed to 10.0 g, the compound (16-1) was changed to the compound (18-1) obtained in Ex. 7-1, the amount of HOCH$_2$C(CH$_2$OCH$_2$CH=CH$_2$)$_3$ was changed to 1.6 g, and no dilution with AK-225 was conducted after completion of the reaction.

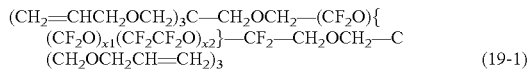
(19-1)

NMR spectrum of compound (19-1);
$^1$H-NMR (300.4 MHz, solvent: CDCl$_3$, reference: TMS) δ (ppm): 3.6 (12H), 3.7 to 3.9 (20H), 5.1 (12H), 5.8 (6H).
$^{19}$F-NMR (282.7 MHz, solvent: CDCl$_3$, reference: C$_6$F$_6$) δ (ppm): −51.2 to −54.6 (42F), −74.1 (6F), −77.3 (2F), −79.2 (2F), −87.5 to −91.0 (80F).

Mean value of the unit number x1: 21, mean value of the unit number x2: 20, number average molecular weight of the compound (19-1): 4,360.

Ex. 7-3

In the same manner as in Ex. 1-8 except that the compound (17-1) was changed to 1.0 g of the compound (19-1)

obtained in Ex. 7-2 and the amount of HSi(OCH$_3$)$_3$ was changed to 0.40 g, 1.1 g (yield: 96%) of a composition (7) comprising compound (2A-1) wherein six allyl groups in the compound (19-1) were hydrosilylated and a by-product wherein some or all of six allyl groups in the compound (19-1) were isomerized to an inner olefin (—CH=CHCH$_3$), was obtained. The conversion in the hydrosilylation was 100%, and no compound (19-1) remained. The selectivity in the hydrosilylation was 84%.

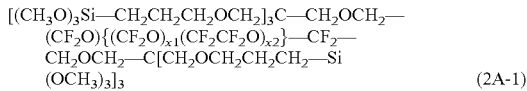
[(CH$_3$O)$_3$Si—CH$_2$CH$_2$CH$_2$OCH$_2$]$_3$C—CH$_2$OCH$_2$—(CF$_2$O){(CF$_2$O)$_{x1}$(CF$_2$CF$_2$O)$_{x2}$}—CF$_2$—CH$_2$OCH$_2$—C[CH$_2$OCH$_2$CH$_2$CH$_2$—Si(OCH$_3$)$_3$]$_3$     (2A-1)

NMR spectrum of compound (2A-1);
$^1$H-NMR (300.4 MHz, solvent: CDCl$_3$, reference: TMS) δ (ppm): 0.7 (12H), 1.7 (12H), 3.4-3.8 (86H).
$^{19}$F-NMR (282.7 MHz, solvent: CDCl$_3$, reference: C$_6$F$_6$) δ (ppm): −51.2 to −54.6 (42F), −77.7 (2F), −79.7 (2F), −87.5 to −91.0 (80F).
Mean value of the unit number x1: 21, mean value of the unit number x2: 20, number average molecular weight of the compound (2A-1): 5,010.

Ex. 8: Production of Compound (4-1)

Ex. 8-1

21.5 g (yield: 98%) of compound (22-1) was obtained in the same manner as in Ex. 1-6 except that the compound (15-1) was changed to the compound (21-1) (manufactured by SynQuest Laboratories), the amount of CF$_3$SO$_2$Cl (manufactured by Wako Pure Chemical Industries, Ltd.) was changed to 4.0 g, and the amount of triethylamine was changed to 4.5 g.

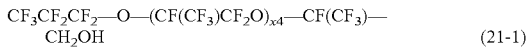
CF$_3$CF$_2$CF$_2$—O—(CF(CF$_3$)CF$_2$O)$_{x4}$—CF(CF$_3$)—CH$_2$OH     (21-1)

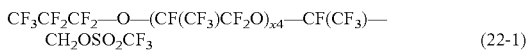
CF$_3$CF$_2$CF$_2$—O—(CF(CF$_3$)CF$_2$O)$_{x4}$—CF(CF$_3$)—CH$_2$OSO$_2$CF$_3$     (22-1)

NMR spectrum of compound (22-1);
$^1$H-NMR (300.4 MHz, solvent: CDCl$_3$, reference: TMS) δ (ppm): 4.9 (2H).
$^{19}$F-NMR (282.7 MHz, solvent: CDCl$_3$, reference: C$_6$F$_6$) δ (ppm): −74.2 (3F), −78.4 to −82.2 (38F), −129.4 (2F), −135.0 (1F), −144.2 (6F).
Mean value of the unit number x4: 6, number average molecular weight of the compound (22-1): 1,440.

Ex. 8-2

2.1 g (yield: 20%) of compound (23-1) was obtained in the same manner as in Ex. 1-7 except that the amount of sodium hydride (55%/paraffin) was changed to 0.05 g, the compound (16-1) was changed to the compound (22-1) obtained in Ex. 8-1, the amount of HOCH$_2$C(CH$_2$OCH$_2$CH=CH$_2$)$_3$ was changed to 0.31 g, and no dilution with AK-225 was conducted after the completion of the reaction.

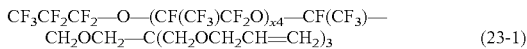
CF$_3$CF$_2$CF$_2$—O—(CF(CF$_3$)CF$_2$O)$_{x4}$—CF(CF$_3$)—CH$_2$OCH$_2$—C(CH$_2$OCH$_2$CH=CH$_2$)$_3$     (23-1)

NMR spectrum of compound (23-1);
$^1$H-NMR (300.4 MHz, solvent: CDCl$_3$, reference: TMS) δ (ppm): 3.6 (6H), 3.7 to 3.9 (8H), 4.0 (2H), 5.1 (6H), 5.8 (3H).

$^{19}$F-NMR (282.7 MHz, solvent: CDCl$_3$, reference: C$_6$F$_6$) δ (ppm): −78.4 to −82.2 (38F), −129.4 (2F), −132.0 (1F), −144.2 (6F).
Mean value of the unit number x4: 6, number average molecular weight of the compound (23-1): 1,550.

Ex. 8-3

In the same manner as in Ex. 1-8 except that the compound (17-1) was changed to the compound (23-1) obtained in Ex. 8-2, the amount of the platinum complex solution was changed to 0.006 g, the amount of HSi(OCH$_3$)$_3$ was changed to 66 g, and the amount of dimethyl sulfoxide was changed to 0.01 g, 2.1 g (yield: 85%) of a composition (8) comprising compound (4-1) wherein three allyl groups in the compound (23-1) were hydrosilylated, and a by-product wherein some or all of three allyl groups in the compound (23-1) were isomerized to an inner olefin (—CH=CHCH$_3$), was obtained. The conversion in the hydrosilylation was 100%, and no compound (23-1) remained. The selectivity in the hydrosilylation was 85%.

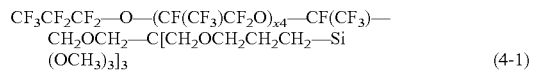
CF$_3$CF$_2$CF$_2$—O—(CF(CF$_3$)CF$_2$O)$_{x4}$—CF(CF$_3$)—CH$_2$OCH$_2$—C[CH$_2$OCH$_2$CH$_2$CH$_2$—Si(OCH$_3$)$_3$]$_3$     (4-1)

NMR spectrum of compound (4-1);
$^1$H-NMR (300.4 MHz, solvent: CDCl$_3$, reference: TMS) δ (ppm): 0.7 (6H), 1.7 (6H), 3.4-3.8 (41H), 4.0 (2H).
$^{19}$F-NMR (282.7 MHz, solvent: CDCl$_3$, reference: C$_6$F$_6$) δ (ppm): −78.4 to −82.2 (38F), −129.4 (2F), −132.0 (1F), −144.2 (6F).
Mean value of the unit number x4: 6, number average molecular weight of the compound (4-1): 1,920.

Ex. 9: Production of Compound (5-1)

Ex. 9-1

Into a 100 mL two-necked eggplant flask, 20.0 g of the compound (15-1) obtained in Ex. 1-5, 0.21 g of tetrabutyl ammonium hydrogen sulfate, 1.76 g of BrCH$_2$CH=CH$_2$ and 2.6 g of a 30% sodium hydroxide solution were added and stirred at 60° C. for 8 hours. After completion of the reaction, 20 g of AC-2000 was added, followed by washing once with dilute aqueous hydrochloric acid, whereupon the organic phase was collected. The collected organic phase was passed through a silica gel column, whereupon the collected solution was concentrated by an evaporator to obtain 19.8 g (yield: 98.2%) of compound (24-1).

CF$_3$CF$_2$CF$_2$—O—(CF$_2$CF$_2$O)(CF$_2$CF$_2$O){(CF$_2$O)$_{x1}$(CF$_2$CF$_2$O)$_{x2}$}—CF$_2$—CH$_2$OCH$_2$CH=CH$_2$     (24-1).

NMR spectrum of compound (24-1);
$^1$H-NMR (300.4 MHz, solvent: CDCl$_3$, reference: TMS) δ (ppm): 3.7 (2H), 4.1 (2H), 5.2 to 5.3 (2H), 5.9 (1H).
$^{19}$F-NMR (282.7 MHz, solvent: CDCl$_3$, reference: CFCl$_3$) δ (ppm): −52.3 to −55.7 (42F), −78.1 (1F), −80.1 (1F), −82.1 (3F), −89.4 to −91.1 (90F), −30.5 (2F).
Mean value of the unit number x1: 21, mean value of the unit number x2: 20, number average molecular weight of the compound (24-1): 4,250.

Ex. 9-2

In the same manner as in Ex. 1-8 except that the compound (17-1) was changed to 5.0 g of the compound (24-1) obtained in Ex. 9-1, the amount of the platinum complex solution was changed to 0.005 g, the amount of HSi(OCH$_3$)$_3$ was changed to 0.25 g, the amount of dimethyl sulfoxide was changed to 0.005 g, the amount of 1,3-bis(trifluoromethyl)benzene (manufactured by Tokyo Chemical Industry Co., Ltd.) was changed to 0.20 g, and the reaction time was changed to 4 hours, 4.9 g (yield: 95%) of a composition (9) comprising the compound (5-1) wherein one allyl group in the compound (24-1) was hydrosilylated and a by-product wherein one allyl group in the compound (24-1) was isomerized to an inner olefin (—CH═CHCH$_3$), was obtained. The conversion in the hydrosilylation was 100%, and no compound (24-1) remained. The selectivity in the hydrosilylation was 87%.

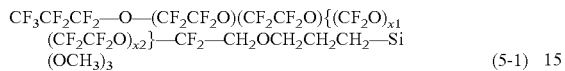
                                                                    (5-1)

NMR spectrum of compound (5-1);
$^1$H-NMR (300.4 MHz, solvent: CDCl$_3$, reference: TMS) δ (ppm): 0.7 (6H), 1.7 (6H), 3.6 (11H), 3.8 (2H).
$^{19}$F-NMR (282.7 MHz, solvent: CDCl$_3$, reference: C$_6$F$_6$) δ (ppm): −52.4 to −55.8 (42F), −78.2 (1F), −80.2 (1F), −82.2 (3F), −89.4 to −91.1 (90F), −130.5 (2F).

Mean value of the unit number x1: 21, mean value of the unit number x2: 20, number average molecular weight of the compound (5-1): 4,370.

Ex. 10: Production of Compound (5-2)

Ex. 10-1

52.4 g (yield: 99.9%) of compound (24-2) was obtained in the same manner as in Ex. 9-1 except that the compound (15-1) was changed to 52.0 g of the compound (11-1) obtained in Ex. 1-1, the amount of tetrabutylammonium hydrogen sulfate was changed to 0.52 g, the amount of BrCH$_2$CH═CH$_2$ was changed to 4.4 g, the amount of the 30% sodium hydroxide aqueous solution was changed to 6.5 g, and the amount of AC-2000 was changed to 50 g.

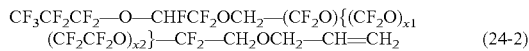
                                                                    (24-2)

NMR spectrum of compound (24-2);
$^1$H-NMR (300.4 MHz, solvent: CDCl$_3$, reference: TMS) δ (ppm): 3.7 (2H), 4.1 (2H), 4.2 (2H), 5.2 to 5.3 (2H), 5.8 to 6.0 (2H).
$^{19}$F-NMR (282.7 MHz, solvent: CDCl$_3$, reference: CFCl$_3$) δ (ppm): −52.3 to −55.7 (42F), −78.1 (1F), −78.7 (1F), −80.2 (1F), −80.7 (1F), −82.2 (3F), −85.4 to −88.2 (2F), −89.4 to −91.1 (86F), −130.5 (2F), −145.1 (1F).

Mean value of the unit number x1: 21, mean value of the unit number x2: 20, number average molecular weight of the compound (24-2): 4,190.

Ex. 10-2

In the same manner as in Ex. 9-2 except that the compound (24-1) was changed to the compound (24-2) obtained in Ex. 10-1, 4.8 g (yield: 93%) of a composition (10) comprising compound (5-2) wherein one allyl group in the compound (24-2) was hydrosilylated and a by-product wherein one allyl group in the compound (24-2) was isomerized to an inner olefin (—CH═CHCH$_3$), was obtained. The conversion in the hydrosilylation was 100%, and no compound (24-2) remained. The selectivity in the hydrosilylation was 85%.

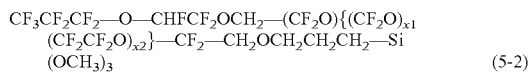
                                                                    (5-2)

NMR spectrum of compound (5-2);
$^1$H-NMR (300.4 MHz, solvent: CDCl$_3$, reference: TMS) δ (ppm): 0.7 (6H), 1.7 (6H), 3.6 (11H), 3.8 (2H), 4.2 (2H), 5.8 to 6.0 (1H).
$^{19}$F-NMR (282.7 MHz, solvent: CDCl$_3$, reference: C$_6$F$_6$) δ (ppm): −52.3 to −55.7 (42F), −78.2 (1F), −78.7 (1F), −80.3 (1F), −80.7 (1F), −82.2 (3F), −85.4 to −88.2 (2F), −89.4 to −91.1 (82F), −130.5 (2F), −45.1 (1F).

Mean value of the unit number x1: 21, mean value of the unit number x2: 20, number average molecular weight of the compound (5-2): 4,310.

Ex. 11: Production of Compound (1I-1)

Ex. 11-1

In accordance with the method described in Example 6 of WO2013/121984, compound (14I-1) was obtained.

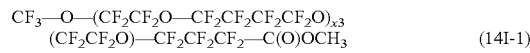
                                                                    (14I-1)

NMR spectrum of compound (14I-1);
$^1$H-NMR (300.4 MHz, solvent: CDCl$_3$, reference: TMS) δ (ppm): 3.9 (3H).
$^{19}$F-NMR (282.7 MHz, solvent: CDCl$_3$, reference: CFCl$_3$) δ (ppm): −55.2 (3F), −82.1 (54F), −88.1 (54F), −90.2 (2F), −118.2 (2F), −125.4 (52F), −126.2 (2F).

Mean value of the unit number x3: 13, number average molecular weight of the compound (14I-1): 4,700.

Ex. 11-2

Into a 50 mL eggplant flask, 9.0 g of the compound (14I-1) obtained in Ex. 11-1 and 0.45 g of H$_2$N—CH$_2$—C(CH$_2$CH═CH$_2$)$_3$ were put and stirred for 12 hours. From NMR, it was confirmed that the compound (14I-1) was all converted to compounds (17I-1). Further, methanol was formed as a by-product. The obtained solution was diluted with 9.0 g of AE-3000, and purified by silica gel column chromatography (developing solvent: AE-3000) to obtain 7.6 g (yield: 84%) of compound (17I-1).

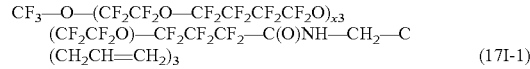
                                                                    (17I-1)

NMR spectrum of compound (17I-1);
$^1$H-NMR (300.4 MHz, solvent: CDCl$_3$, reference: TMS) δ (ppm): 2.1 (6H), 3.4 (2H), 5.2 (6H), 6.2 to 5.9 (3H).
$^{19}$F-NMR (282.7 MHz, solvent: CDCl$_3$, reference: CFCl$_3$) δ (ppm): −55.2 (3F), −82.1 (54F), −88.1 (54F), −90.2 (2F), −119.6 (2F), −125.4 (52F), −126.2 (2F).

Mean value of the unit number x3: 13, number average molecular weight of the compound (17I-1): 4,800.

Ex. 11-3

Into a 10 mL sample tube made of PFA, 6.0 g of the compound (17I-1) obtained in Ex. 11-2, 0.07 g of a xylene solution (platinum content: 2%) of platinum/1,3-divinyl-1,1,3,3-tetramethyl disiloxane complex, 0.78 g of HSi(OCH$_3$)$_3$, 0.02 g of dimethyl sulfoxide, and 0.49 g of 1,3-bis(trifluoromethyl)benzene (manufactured by Tokyo Chemical Industry Co., Ltd.) were put and stirred at 40° C. for 10 hours. After completion of the reaction, the solvent, etc. were distilled off under reduced pressure, followed by filtration through a membrane filter of 1.0 μm pore size, to obtain 6.7 g (yield: 100%) of compound (1I-1).

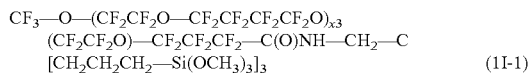
(1I-1)

NMR spectrum of compound (1I-1);
$^1$H-NMR (300.4 MHz, solvent: CDCl$_3$, reference: TMS) δ (ppm): 0.75 (6H), 1.3 to 1.6 (12H), 3.4 (2H), 3.7 (27H).
$^{19}$F-NMR (282.7 MHz, solvent: CDCl$_3$, reference: CFCl$_3$) δ (ppm): −55.2 (3F), −82.1 (54F), −88.1 (54F), −90.2 (2F), −119.6 (2F), −25.4 (52F), −26.2 (2F).

Mean value of the unit number x3: 13, number average molecular weight of the compound (1I-1): 5,400.

Ex. 12: Production of Compound (1I-2)

Ex. 12-1

7.5 g (yield: 84%) of compound (17I-2) was obtained in the same manner as in Ex. 11-2 except that instead of 0.45 g of H$_2$N—CH$_2$—C(CH$_2$CH═CH$_2$)$_3$, 0.41 g of H$_2$N—C(CH$_2$CH═CH$_2$)$_3$ was used.

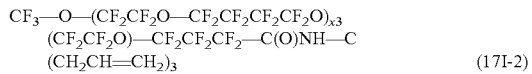
(17I-2)

NMR spectrum of compound (17I-2);
$^1$H-NMR (300.4 MHz, solvent: CDCl$_3$, reference: TMS) δ (ppm): 2.3 (6H), 5.2 (6H), 5.9 to 6.2 (3H).
$^{19}$F-NMR (282.7 MHz, solvent: CDCl$_3$, reference: CFCl$_3$) δ (ppm): −55.2 (3F), −82.1 (54F), −88.1 (54F), −90.2 (2F), −119.4 (2F), −125.4 (52F), −126.2 (2F).

Mean value of the unit number x3: 13, number average molecular weight of the compound (17I-2): 4,800.

Ex. 12-2

6.7 g (yield: 100%) of compound of (1I-2) was obtained in the same manner as in Ex. 11-3 except that instead of the compound (17I-1), the compound (17I-2) obtained in Ex. 12-1 was used.

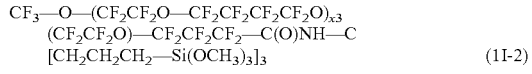
(1I-2)

NMR spectrum of compound (1I-2);
$^1$H-NMR (300.4 MHz, solvent: CDCl$_3$, reference: TMS) δ (ppm): 0.75 (6H), 1.3 to 1.6 (12H), 3.7 (27H).
$^{19}$F-NMR (282.7 MHz, solvent: CDCl$_3$, reference: CFCl$_3$) δ (ppm): −55.2 (3F), −82.1 (54F), −88.1 (54F), −90.2 (2F), −119.4 (2F), −125.4 (52F), −126.2 (2F).

Mean value of the unit number x3: 13, number average molecular weight of the compound (1I-2): 5,400.

Ex. 13: Production of Compound (IH-1)

Ex. 13-1

In accordance with the method described in J. Org. Chem., Vol. 64, 1999, p. 2564-2566, the compound (1I-1) obtained in Ex. 1-1 was oxidized to obtain compound (13H-1).

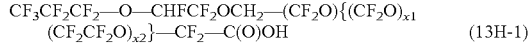
(13H-1)

NMR spectrum of compound (13H-1),
$^1$H-NMR (300.4 MHz, solvent: CDCl$_3$, reference: TMS) δ (ppm): 4.2 (2H), 5.8 to 6.0 (1H).
$^{19}$F-NMR (282.7 MHz, solvent: CDCl$_3$, reference: CFCl$_3$) δ (ppm): −52.4 to −55.8 (42F), −78.8 (2F), −80.5 (1F), −80.8 (1F), −82.2 (3F), −85.3 to −88.2 (2F), −89.4 to −91.1 (82F), −130.5 (2F), −145.1 (1F).

Mean value of the unit number x1: 21, mean value of the unit number x2: 20, number average molecular weight of the compound (13H-1): 4,150.

Ex. 13-2

Into a 50 mL eggplant flask, 6.2 g of the compound (13H-1) obtained in Ex. 13-1 and 20 mL of methanol were put and stirred at room temperature for 12 hours. From NMR, it was confirmed that the compound (13H-1) was all converted to compound (14H-1). By distilling off the solvent under reduced pressure, 6.2 g (yield: 100%) of the compound (14H-1) was obtained.

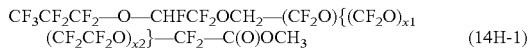
(14H-1)

NMR spectrum of compound (14H-1);
$^1$H-NMR (300.4 MHz, solvent: CDCl$_3$, reference: TMS) δ (ppm): 3.9 (3H), 4.2 (2H), 5.8 to 6.0 (1H).
$^{19}$F-NMR (282.7 MHz, solvent: CDCl$_3$, reference: CFCl$_3$) δ (ppm): −52.4 to −55.8 (42F), −77.8 (1F), −78.8 (1F), −79.5 (1F), −80.8 (1F), −82.2 (3F), −85.3 to −88.2 (2F), −89.4 to −91.1 (82F), −130.5 (2F), −145.1 (1F).

Mean value of the unit number x1: 21, mean value of the unit number x2: 20, number average molecular weight of the compound (14H-1): 4,150.

Ex. 13-3

4.8 g (yield: 76%) of the compound (17H-1) was obtained in the same manner as in Ex. 11-2 except that the compound (14I-1) was changed to 5.7 g of the compound (14H-1) obtained in Ex. 13-2, and the amount of H$_2$N—CH$_2$—C(CH$_2$CH═CH$_2$)$_3$ was changed to 0.26 g.

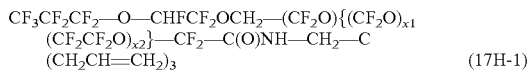
(17H-1)

NMR spectrum of compound (17H-1);
$^1$H-NMR (300.4 MHz, solvent: CDCl$_3$, reference: TMS) δ (ppm): 2.2 (6H), 3.3 (2H), 3.5 (1H), 4.2 (2H), 5.2 (6H), 5.8 to 6.0 (4H).
$^{19}$F-NMR (282.7 MHz, solvent: CDCl$_3$, reference: CFCl$_3$) δ (ppm): −52.4 to −55.8 (42F), −78.8 (2F), −79.6 (1F), −80.8 (1F), −82.2 (3F), −85.3 to −88.2 (2F), −89.4 to −91.1 (82F), −130.5 (2F), −145.1 (1F).

Mean value of the unit number x1: 21, mean value of the unit number x2: 20, number average molecular weight of the compound (17H-1): 4,250.

Ex. 13-4

3.8 g (yield: 100%) of compound (1H-1) was obtained in the same manner as in Ex. 11-3 except that the compound (17I-1) was changed to 3.5 g of the compound (17H-1) obtained in Ex. 13-3, the amount of the platinum complex solution was changed to 0.03 g, the amount of HSi(OCH$_3$)$_3$ was changed to 0.5 g, the amount of dimethyl sulfoxide was changed to 0.01 g, and the amount of 1,3-bis(trifluoromethyl)benzene (manufactured by Tokyo Chemical Industry Co., Ltd.) was changed to 0.35 g.

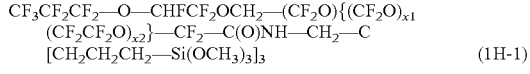
(1H-1)

NMR spectrum of compound (1H-1);
¹H-NMR (300.4 MHz, solvent: CDCl₃, reference: TMS) δ (ppm): 0.75 (6H), 1.3 to 1.6 (12H), 3.4 (2H), 3.7 (27H), 5.8 to 6.0 (1H).
¹⁹F-NMR (282.7 MHz, solvent: CDCl₃, reference: CFCl₃) δ (ppm): −52.4 to −55.8 (42F), −78.8 (2F), −79.6 (1F), −80.8 (1F), −82.2 (3F), −85.3 to −88.2 (2F), −89.4 to −91.1 (82F), −130.5 (2F), −145.1 (1F).

Mean value of the unit number x1: 21, mean value of the unit number x2: 20, number average molecular weight of the compound (1H-1): 4,600.

Ex. 14: Production of Compound (1H-2)

Ex. 14-1

4.7 g (yield: 80%) of compound (17H-2) was obtained in the same manner as in Ex. 13-3 except that instead of 0.26 g of H₂N—CH₂—C(CH₂CH=CH₂)₃, 0.24 g of H₂N—C(CH₂CH=CH₂)₃ was used.

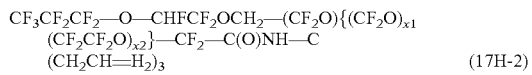

NMR spectrum of compound (17H-2);
¹H-NMR (300.4 MHz, solvent: CDCl₃, reference: TMS) δ (ppm): 2.4 (6H), 3.5 (1H), 5.2 (6H), 5.8 to 6.0 (4H).
¹⁹F-NMR (282.7 MHz, solvent: CDCl₃, reference: CFCl₃) δ (ppm): −52.4 to −55.8 (42F), −78.8 (2F), −79.6 (1F), −80.8 (1F), −82.2 (3F), −85.3 to −88.2 (2F), −89.4 to −91.1 (82F), −130.5 (2F), −145.1 (1F).

Mean value of the unit number x1: 21, mean value of the unit number x2: 20, number average molecular weight of the compound (17H-2): 4,250.

Ex. 14-2

3.8 g (yield: 100%) of compound (1H-2) was obtained in the same manner as Ex. 13-4 except that the compound (17H-1) was changed to the compound (17H-2) obtained in Ex. 14-1.

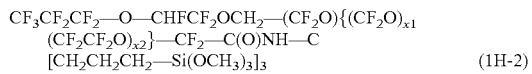

NMR spectrum of compound (1H-2);
¹H-NMR (300.4 MHz, solvent: CDCl₃, reference: TMS) δ (ppm): 0.75 (6H), 1.3 to 1.7 (12H), 3.4 (2H), 3.7 (27H), 5.8 to 6.0 (1H).
¹⁹F-NMR (282.7 MHz, solvent: CDCl₃, reference: CFCl3) δ (ppm): −52.4 to −55.8 (42F), −78.8 (2F), −79.6 (1F), −80.8 (1F), −82.2 (3F), −85.3 to −88.2 (2F), −89.4 to −91.1 (82F), −130.5 (2F), −145.1 (1F).

Mean value of the unit number x1: 21, mean value of the unit number x2: 20, number average molecular weight of the compound (1H-2): 4,600.

Ex. 15: Production of Compound (1 K-1)

Ex. 15-1

Into a 50 mL eggplant flask, 1.0 g of CF₂=CFOCF₂CF₂CF₂—C(O)OCH₃ and 0.55 g of H₂N—CH₂—C(CH₂CH=CH₂)₃ were put and stirred for 12 hours. From NMR, it was confirmed that CF₂=CFOCF₂CF₂CF₂—C(O)OCH₃ was all converted to compound (30-1). Further, methanol was formed as a by-product. The obtained solution was diluted with 6.0 g of AE-3000, followed by purification by silica gel column chromatography (developing solvent: AE-3000) to obtain 1.3 g (yield: 84%) of the compound (30-1).

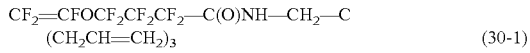

NMR spectrum of compound (30-1);
¹H-NMR (300.4 MHz, solvent: CDCl₃, reference: TMS) δ (ppm): 2.1 (6H), 3.4 (2H), 5.2 (6H), 5.9 to 6.2 (3H).
¹⁹F-NMR (282.7 MHz, solvent: CDCl₃, reference: CFCl₃) δ (ppm): −84.2 (2F), −113.4 to 114.2 (1F), −119.5 (2F), −121.1 to −121.9 (1F), −125.3 (2F), −134.5 to −135.3 (1F).

Ex. 15-2

Into a 50 mL eggplant flask, 1.0 g of the compound (30-1) obtained in Ex. 15-1, 10 g of the compound (11-1) obtained in Ex. 1-1, 2 g of a 48 mass % potassium hydroxide aqueous solution, and 0.1 g of (CH₃)₃COH, were added and stirred at 60° C. for 5 hours. From NMR, it was confirmed that the compound (11-1) was all converted to compound (17K-1). To the obtained solution, 20 g of 1N hydrochloric acid was added, and after confirming that the aqueous layer became acidic, the organic layer was separated and the solvent was distilled off, to obtain 11 g (yield: 100%) of the compound (17K-1).

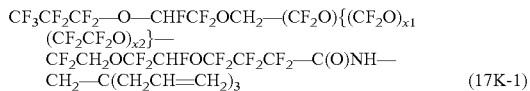

NMR spectrum of compound (17K-1);
¹H-NMR (300.4 MHz, solvent: CDCl₃, reference: TMS) δ (ppm): 2.2 (6H), 3.3 (2H), 3.5 (1H), 4.2 (4H), 5.2 (6H), 5.8 to 6.0 (5H).
¹⁹F-NMR (282.7 MHz, solvent: CDCl₃, reference: CFCl₃) δ (ppm): −52.4 to −55.8 (42F), −78.8 (2F), −79.6 (1F), −80.8 (1F), −82.2 (3F), −84.2 (2F), −85.3 to −88.2 (2F), −89.4 to −91.1 (82F), −119.5 (2F), −125.3 (2F), −130.5 (4F), −145.1 (2F).

Mean value of the unit number x1: 21, mean value of the unit number x2: 20, number average molecular weight of the compound (17K-1): 4,520.

Ex. 15-3

5.4 g (yield: 100%) of compound (1K-1) was obtained in the same manner as in Ex. 11-3 except that the compound (17I-1) was changed to 5 g of the compound (17K-1) obtained in Ex. 15-2, the amount of the platinum complex solution was changed to 0.5 mg, the amount of HSi(OCH₃)₃ was changed to 0.5 g, the amount of dimethyl sulfoxide was changed to 0.01 g, and the amount of 1,3-bis(trifluoromethyl)benzene (manufactured by Tokyo Chemical Industry Co., Ltd.) was changed to 0.2 g.

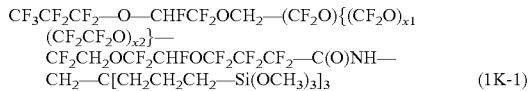

NMR spectrum of compound (1K-1);
¹H-NMR (300.4 MHz, solvent: CDCl₃, reference: TMS) δ (ppm): 0.75 (6H), 1.3 to 1.6 (12H), 3.3 (2H), 3.5 (27H), 4.2 (4H), 5.8 to 6.0 (2H).
¹⁹F-NMR (282.7 MHz, solvent: CDCl₃, reference: CFCl₃) δ (ppm): −52.4 to −55.8 (42F), −78.8 (2F), −79.6

(1F), −80.8 (1F), −82.2 (3F), −84.2 (2F), −85.3 to −88.2 (2F), −89.4 to −91.1 (82F), −119.5 (2F), −125.3 (2F), −130.5 (4F), −145.1 (2F).

Mean value of the unit number x1: 21, mean value of the unit number x2: 20, number average molecular weight of the compound (1K-1): 4,950.

Ex. 16: Production of Compound (1 G-1)

Ex. 16-1

In accordance with the method described in Example 4 in WO2014/163004, compound (14-1) was obtained.

(14-1)

NMR spectrum of compound (14-1);
$^1$H-NMR (300.4 MHz, solvent: CDCl$_3$, reference: TMS) δ (ppm): 3.9 (3H).
$^{19}$F-NMR (282.7 MHz, solvent: CDCl$_3$, reference: CFCl$_3$) δ (ppm): −52.4 to −55.8 (42F), −82.2 (3F), −89.4 to −91.1 (92F), −130.5 (2F).

Mean value of the unit number x1: 21, mean value of the unit number x2: 20, number average molecular weight of the compound (14-1): 4,230.

Ex. 16-2

4.4 g (yield: 85%) of compound (17G-1) was obtained in the same manner as in Ex. 11-2 except that the compound (14I-1) was changed to 5.0 g of the compound (14-1) obtained in Ex. 16-1, and the amount of H$_2$N—CH$_2$—C(CH$_2$CH=CH$_2$)$_3$ was changed to 0.2 g.

(17G-1)

NMR spectrum of compound (17G-1);
$^1$H-NMR (300.4 MHz, solvent: CDCl$_3$, reference: TMS) δ (ppm): 2.2 (6H), 3.3 (2H), 3.5 (1H), 5.2 (6H), 5.8 to 6.0 (3H).
$^{19}$F-NMR (282.7 MHz, solvent: CDCl$_3$, reference: CFCl$_3$) δ (ppm): −52.4 to −55.8 (42F), −82.2 (3F), −89.4 to −91.1 (92F), −130.8 (2F).

Mean value of the unit number x1: 21, mean value of the unit number x2: 20, number average molecular weight of the compound (17G-1): 4,360.

Ex. 16-3

4.3 g (yield: 100%) of compound (1G-1) was obtained in the same manner as in Ex. 11-3 except that the compound (17I-1) was changed to 4 g of the compound (17G-1) obtained in Ex. 16-2, the amount of the platinum complex solution was changed to 0.4 mg, the amount of HSi(OCH$_3$)$_3$ was changed to 0.33 g, the amount of dimethyl sulfoxide was changed to 0.01 g, and the amount of 1,3-bis(trifluoromethyl)benzene (manufactured by Tokyo Chemical Industry Co., Ltd.) was changed to 0.2 g.

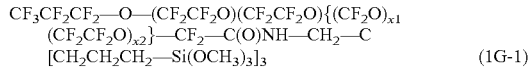

(1G-1)

NMR spectrum of compound (1 G-1);
$^1$H-NMR (300.4 MHz, solvent: CDCl$_3$, reference: TMS) δ (ppm): 0.75 (6H), 1.3 to 1.6 (12H), 3.4 (2H), 3.7 (27H).
$^{19}$F-NMR (282.7 MHz, solvent: CDCl$_3$, reference: CFCl$_3$) δ (ppm): −52.4 to −55.8 (42F), −82.2 (3F), −89.4 to −91.1 (92F), −130.8 (2F).

Mean value of the unit number x1: 21, mean value of the unit number x2: 20, number average molecular weight of the compound (1 G-1): 4,720.

Ex. 48: Production of Compound (1D-2)

Ex. 48-1

Into a 50 mL three-necked flask, 3.0 g of pentaerythritol (manufactured by Kanto Chemical Co., Inc.), 7.4 g of a 48% NaOH aqueous solution and 10.8 g of dimethyl sulfoxide were put and heated to 60° C., then, 11.5 g of 5-bromo-1-pentene (manufactured by Tokyo Chemical Industry Co., Ltd.) was added and stirred for 4 hours. After washing once with dilute aqueous hydrochloric acid, 16 g of cyclopentyl methyl ether (manufactured by Kanto Chemical Co., Inc.) was added, and an organic phase was collected. The collected solution was concentrated by an evaporator to obtain 6.1 g of a crude product. The crude product was developed by silica gel column chromatography (developing solvent: hexane/ethyl acetate=90/10 (mass ratio)), to fractionate 3.7 g (yield: 49%) of HOCH$_2$C(CH$_2$OCH$_2$CH$_2$CH=CH$_2$)$_3$.

Ex. 48-2

Into a 50 mL eggplant flask, 3.0 g of HOCH$_2$C(CH$_2$OCH$_2$CH$_2$CH=CH$_2$)$_3$ obtained in Ex. 48-1, 9.0 g of AE-3000 and 1.4 g of 2,6-lutidine were put, and under a nitrogen atmosphere, 3.8 g of (CF$_3$SO$_2$)$_2$O was dropwise added at 0° C. The mixture was heated to room temperature and stirred for 1 hour. After completion of the reaction, washing with water was conducted, whereupon the organic phase was collected and concentrated by an evaporator. The concentrate was purified by silica gel column chromatography (developing solvent: AE-3000) to obtain 4.2 g (yield: 99%) of compound (20-2).

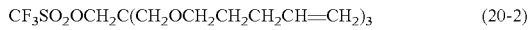

(20-2)

NMR spectrum of compound (20-2);
$^1$H-NMR (300.4 MHz, solvent: CDCl$_3$, reference: TMS) δ (ppm): 1.6 (6H), 2.0 (6H), 3.4 (12H), 4.5 (2H), 5.0 (6H), 5.8 (3H).
$^{19}$F-NMR (282.7 MHz, solvent: CDCl$_3$, reference: C$_6$F$_6$) δ (ppm): −75.0 (3F).

Ex. 48-3

In a 25 mL eggplant flask, 8.9 g of the compound (15-1) obtained in Ex. 1-5, 1.0 g of the compound (20-2) obtained in Ex. 48-2, 11 g of 1,3-bis(trifluoromethyl)benzene and 1.4 g of cesium carbonate were put and stirred at 80° C. for 8 hours under a nitrogen atmosphere. After completion of the reaction, washing with water was conducted, whereupon the organic phase was collected and concentrated by an evaporator. The concentrate was purified by silica gel column chromatography (developing solvent: AE-3000, followed by AE-3000/ethyl acetate=9/1 (mass ratio)) to obtain 8.2 g (yield: 85%) of compound (17D-2).

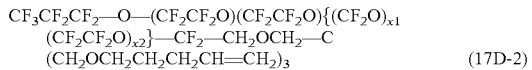

(17D-2)

NMR spectrum of compound (17D-2);
$^1$H-NMR (300.4 MHz, solvent: CDCl$_3$, reference: TMS) δ (ppm): 1.6 (6H), 2.1 (6H), 3.4 (6H), 3.5 (6H), 3.7 (2H), 3.9 (2H), 4.8 to 5.0 (6H), 5.8 (3H).

$^{19}$F-NMR (282.7 MHz, solvent: CDCl$_3$, reference: CFCl$_3$) δ (ppm): −52.4 to −55.7 (42F), −77.2 (1F), −79.4 (1F), −82.2 (3F), −89.4 to −91.1 (90F), −130.5 (2F).

Mean value of the unit number x1: 21, mean value of the unit number x2: 20, number average molecular weight of the compound (17D-2): 4,540.

Ex. 48-4

In the same manner as in Ex. 1-8 except that the compound (17-1) was changed to the compound (17D-2) obtained in Ex. 48-3, 2.1 g (yield: 97%) of compound (1 D-2) was obtained wherein three vinyl groups in the compound (17D-2) were hydrosilylated. The conversion in the hydrosilylation was 100%, and no compound (17D-2) remained. The selectivity in the hydrosilylation was 100%, and no by-product was formed wherein some or all of three vinyl groups in the compound (17D-2) were isomerized to an inner olefin (—CH═CHCH$_3$).

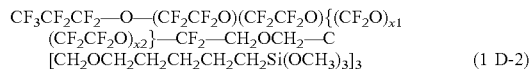
(1 D-2)

NMR spectrum of compound (1 D-2);
$^1$H-NMR (300.4 MHz, solvent: CDCl$_3$, reference: TMS) δ (ppm): 0.7 (6H), 1.4-1.6 (18H), 3.4 (6H), 3.5 (6H), 3.6 (27H), 3.7 (2H), 3.9 (2H).
$^{19}$F-NMR (282.7 MHz, solvent: CDCl$_3$, reference: CFCl$_3$) δ (ppm): −52.3 to −55.6 (42F), −77.2 (1F), −79.4 (1F), −82.2 (3F), −89.4 to −91.0 (90F), −130.5 (2F).

Mean value of the unit number x1: 21, mean value of the unit number x2: 20, number average molecular weight of the compound (1 D-2): 4,900.

Ex. 49: Production of Compound (1E-2)

Ex. 49-1

7.9 g (yield: 83%) of compound (17E-2) was obtained in the same manner as in Ex. 48-3 except that the compound (15-1) was changed to 8.8 g of the compound (11-1) obtained in Ex. 1-1.

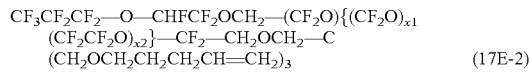
(17E-2)

NMR spectrum of compound (17E-1);
$^1$H-NMR (300.4 MHz, solvent: CDCl$_3$, reference: TMS) δ (ppm): 1.6 (6H), 2.1 (6H), 3.4 (6H), 3.5 (6H), 3.7 (2H), 3.9 (2H), 4.2 (2H), 4.8 to 5.0 (6H), 5.8 to 6.0 (4H).
$^{19}$F-NMR (282.7 MHz, solvent: CDCl$_3$, reference: C$_6$F$_6$) δ (ppm): −51.2 to −54.6 (42F), −77.2 (1F), −77.7 (1F), −79.3 (1F), −79.7 (1F), −81.2 (3F), −84.3 to −87.2 (2F), −87.9 to −91.0 (82F), −129.4 (2F), −144.1 (1F).

Mean value of the unit number x1: 21, mean value of the unit number x2: 20, number average molecular weight of the compound (17E-1): 4,490.

Ex. 49-2

In the same manner as in Ex. 1-8 except that the compound (17D-2) was changed to the compound (17E-2) obtained in Ex. 49-1, 2.0 g (yield: 92%) of compound (1E-2) was obtained wherein three vinyl groups in the compound (17E-2) were hydrosilylated. The conversion in the hydrosilylation was 100%, and no compound (17E-2) remained. The selectivity in the hydrosilylation was 100%, and no by-product was formed wherein some or all of three vinyl groups in the compound (17E-2) were isomerized to an inner olefin (—CH═CHCH$_3$).

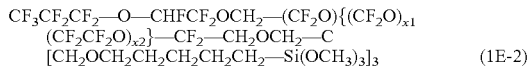
(1E-2)

NMR spectrum of compound (1E-2);
$^1$H-NMR (300.4 MHz, solvent: CDCl$_3$, reference: TMS) δ (ppm): 0.7 (6H), 1.4-1.6 (18H), 3.4 (6H), 3.5 (6H), 3.6 (27H), 3.7 (2H), 3.9 (2H), 4.2 (2H), 5.8 to 6.0 (1H).
$^{19}$F-NMR (282.7 MHz, solvent: CDCl$_3$, reference: C$_6$F$_6$) δ (ppm): −51.2 to −54.6 (42F), −77.2 (1F), −77.7 (1F), −79.3 (1F), −79.7 (1F), −81.2 (3F), −84.3 to −87.2 (2F), −87.9 to −91.0 (82F), −129.4 (2F), −144.1 (1F).

Mean value of the unit number x1: 21, mean value of the unit number x2: 20, number average molecular weight of the compound (1E-2): 4,850.

Ex. 50: Production of Compound (1F-2)

Ex. 50-1

8.8 g (yield: 83%) of compound (17F-2) was obtained in the same manner as in Ex. 48-3 except that the compound (15-1) was changed to 9.9 g of the compound (15C-1) obtained in Ex. 3-1.

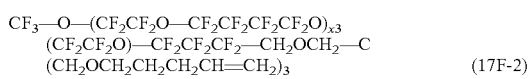
(17F-2)

NMR spectrum of compound (17F-2);
$^1$H-NMR (300.4 MHz, solvent: CDCl$_3$, reference: TMS) δ (ppm): 1.6 (6H), 2.1 (6H), 3.4 (6H), 3.5 (6H), 3.7 (2H), 3.9 (2H), 4.8 to 5.0 (6H), 5.8 (3H).
$^{19}$F-NMR (282.7 MHz, solvent: CDCl$_3$, reference: C$_6$F$_6$) δ (ppm): −56.3 (3F), −84.0 (54F), −89.2 (54F), −91.4 (2F), −120.5 (2F), −126.6 (52F), −128.6 (2F).

Mean value of the unit number x3: 13, number average molecular weight of the compound (17F-2): 5,040.

Ex. 50-2

In the same manner as in Ex. 1-8 except that the compound (17D-2) was changed to the compound (17F-2) obtained in Ex. 50-1, 2.1 g (yield: 98%) of compound (1F-2) was obtained wherein three vinyl groups in the compound (17F-2) were hydrosilylated. The conversion in the hydrosilylation was 100%, and no compound (17F-2) remained. The selectivity in the hydrosilylation was 100%, and no by-product was formed wherein some or all of three vinyl groups in the compound (17F-2) were isomerized to an inner olefin (—CH═CHCH$_3$).

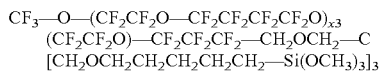
(1F-2)

NMR spectrum of compound (1F-2);
$^1$H-NMR (300.4 MHz, solvent: CDCl$_3$, reference: TMS) δ (ppm): 0.7 (6H), 1.4-1.6 (18H), 3.4 (6H), 3.5 (6H), 3.6 (27H), 3.7 (2H), 3.9 (2H).
$^{19}$F-NMR (282.7 MHz, solvent: CDCl$_3$, reference: C$_6$F$_6$) δ (ppm): −56.3 (3F), −84.0 (54F), −89.2 (54F), −91.4 (2F), −120.5 (2F), −126.6 (52F), −128.6 (2F).

Mean value of the unit number x3: 13, number average molecular weight of the compound (1F-1): 5,400.

Ex. 17 to 32 and 51 to 53: Production and Evaluation of Articles

Surface treatment of a substrate was conducted by using the compound or composition obtained in each of Ex. 1 to16 and 48 to 50, to obtain an article in each of Ex. 17 to 32 and 51 to 53. As the surface treatment method, each of the following dry coating method and wet coating method, was used in each Ex. As the substrate, chemically strengthened glass was used. With respect to the obtained article, evaluations were conducted by the following methods. The results are shown in Tables 1 to 4.

(Dry Coating Method)

Dry coating was conducted by means of a vacuum vapor deposition apparatus (manufactured by ULVAC Co., VTR-350M) (vacuum vapor deposition method). 0.5 g of the compound or composition obtained in each of Ex. 1 to 16 and 48 to 50 was filled into a molybdenum boat in the vacuum vapor deposition apparatus, and inside of the vacuum vapor deposition apparatus was evacuated to a level of at most $1 \times 10^{-3}$ Pa. The boat having the composition placed therein was heated at a temperature raising rate of at most 10° C./min, and at the time when the vapor deposition rate by a quartz oscillator film thickness meter exceeded 1 nm/sec., the shutter was opened to initiate film deposition on the surface of the substrate. At the time when the film thickness became about 50 nm, the shutter was closed to terminate film deposition on the surface of the substrate. The substrate to which the composition was deposited, was heat-treated at 200° C. for 30 minutes, followed by washing with AK-225, to obtain an article having a surface-treated layer on the surface of the substrate.

(Wet Coating Method)

The compound or composition obtained in each of Ex. 1 to 16 and 48 to 50, and $C_4F_9OC_2H_5$ (manufactured by 3M, Novec (registered trademark) 7200) as a liquid medium, were mixed to prepare a coating liquid having a solid content concentration of 0.05%. A substrate was dipped in the coating liquid and allowed to stand for 30 minutes, whereupon the substrate was withdrawn (dip coating method). The coating film was dried at 200° C. for 30 minutes and washed with AK-225, to obtain an article having a surface-treated layer on the surface of the substrate.

(Evaluation Methods)

<Method for Measuring Contact Angle>

A contact angle of about 2 μL of distilled water or n-hexadecane placed on the surface of the surface layer, was measured by using a contact angle measuring apparatus (manufactured by Kyowa Interface Science Co., Ltd. DM-500). Measurements were conducted at five different points on the surface of the surface layer, and the average value was calculated. For the calculation of the contact angle, a 2θ method was employed.

<Initial Contact Angle>

With respect to the surface layer, the initial water contact angle and the initial n-hexadecane contact angle were measured by the above-mentioned measuring method. The evaluation standards are as follows.

Initial water contact angle:

⊚ (excellent): at least 115 degrees.

○ (good): at least 110 degrees and less than 115 degrees.

Δ (acceptable): at least 100 degrees and less than 110 degrees.

× (poor): less than 100 degrees.

Initial n-hexadecane contact angle:

⊚ (excellent): at least 66 degrees.

○ (good): at least 65 degrees and less than 66 degrees.

Δ (acceptable): at least 63 degrees and less than 65 degrees.

× (poor): less than 63 degrees.

<Abrasion Resistance>

With respect to the surface layer, in accordance with JIS L0849: 2013 (ISO 105-X12: 2001), using a reciprocating traverse testing machine (manufactured by KNT Co.), steel wool Bon Star (#0000) was reciprocated 10,000 times under a pressure of 98.07 kPa at a speed of 320 cm/min, to measure the water contact angle. The smaller the decrease in water repellency (water contact angle) after the abrasion, the smaller the decrease in performance due to the abrasion, and the better the abrasion resistance. The evaluation standards are as follows.

⊚ (excellent): The change in water contact angle after reciprocation of 10,000 times is at most 5 degrees.

○ (good): The change in water contact angle after reciprocation of 10,000 times is more than 5 degrees and at most 10 degrees.

Δ (acceptable): The change in water contact angle after reciprocation of 10,000 times is more than 10 degrees and at most 20 degrees.

× (poor): The change in water contact angle after reciprocation of 10,000 is more than 20 degrees.

<Outer Appearance>

The haze of an article was measured by a haze meter (manufactured by Toyo Seiki Seisaku-sho, Ltd.). The smaller the haze, the more uniform the coating of the fluorinated ether compound, and the better the outer appearance. The evaluation standards are as follows.

⊚ (excellent): The haze is at most 0.1%.

○ (good): The haze is more than 0.1% and at most 0.2%.

Δ (acceptable): The haze is more than 0.2% and at most 0.3%.

× (poor): The haze is more than 0.3%.

<Fingerprint Stain Removability>

An artificial fingerprint liquid (liquid consisting of oleic acid and squalene) was deposited on the flat surface of a silicon rubber plug, and extra oil was wiped off by a nonwoven fabric (manufactured by Asahi Kasei Corporation, BEMCOT (registered trademark) M-3), to prepare a stamp for fingerprint. Such a fingerprint stamp was placed on the surface layer and pressed with a load of 9.8N for 10 seconds. The haze at a portion where the fingerprint adhered, was measured by a haze meter, and taken as an initial value. With respect to the portion where the fingerprint adhered, using a reciprocating traverse testing machine (manufactured by KNT Co.) having a tissue paper attached, wiping was conducted with a load of 4.9N. The value of haze was measured every one reciprocation wiping, and the number of wiping times where the haze became at most 10% from the initial value, was measured. The smaller the number of wiping times, the easier the removal of the fingerprint, and the better the fingerprint stain removability. The evaluation standards are as follows.

⊚ (excellent): The number of wiping times is at most 3 times.

○ (good): The number of wiping times is from 4 to 5 times.

Δ (acceptable): The number of wiping times is from 6 to 8 times.

× (poor): The number of wiping times is at least 9 times.

<Light Resistance>

To the surface layer, using a tabletop xenon arc lamp type accelerated light resistance testing machine (manufactured by Toyo Seiki Seisaku-sho, Ltd SUNTEST XLS+), at a black panel temperature of 63° C., light (650 W/m², 300 to 700 nm) was irradiated for 500 hours, whereupon the water contact angle was measured. The smaller the decrease in the water contact angle after the accelerated light resistance test, the smaller the decrease in the performance due to light, and the better the light resistance. The evaluation standards are as follows.

⊚ (excellent): The change in water contact angle after the accelerated light resistance test is at most 5 degrees.

○ (good): The change in water contact angle after the accelerated light resistance test is more than 5 degrees and at most 10 degrees.

Δ (acceptable): The change in water contact angle after the accelerated light resistance test is more than 10 degrees and at most 20 degrees.

× (poor): The change in water contact angle after the accelerated light resistance test is more than 20 degrees.

<Lubricity>

The dynamic friction coefficient of the surface layer to an artificial skin (manufactured by Idemitsu Technofine Co., PBZ13001) was measured by using a load variation type friction wear test system (manufactured by Shinto Scientific Co., Ltd. HHS2000) under conditions of a contact area: 3 cm×3 cm, and a load: 0.98N. The smaller the dynamic friction coefficient, the better the lubricity. The evaluation standards are as follows.

⊚ (excellent): The dynamic friction coefficient is at most 0.3.

○ (good): The dynamic friction coefficient is more than 0.3 and at most 0.4.

Δ (acceptable): The dynamic friction coefficient is more than 0.4 and at most 0.5.

× (poor): The dynamic friction coefficient is more than 0.5.

TABLE 1

| | | | | Ex. | | |
|---|---|---|---|---|---|---|
| | | 17 | 18 | 19 | 20 | 21 |
| Fluorinated ether compound/composition | Type | Composition (1): compound (1A-1) + By-product | Composition (2): compound (1B-1) + By-product | Composition (3): compound (1C-1) + By-product | Compound (1D-1) | Compound (1E-1) |
| | Conversion (%) in hydrosilylation | 100 | 100 | 100 | 100 | 100 |
| | Selectivity (%) in hydrosilylation | 85 | 87 | 85 | 100 | 100 |
| Dry coating method | Initial contact angle Water | ⊚ | ○ | ⊚ | ⊚ | ○ |
| | n-Hexadecane | ⊚ | ⊚ | ⊚ | ⊚ | ⊚ |
| | Abrasion resistance | ○ | ○ | ○ | ⊚ | ⊚ |
| Wet coating method | Initial contact angle Water | ⊚ | ○ | ⊚ | ⊚ | ○ |
| | n-Hexadecane | ⊚ | ⊚ | ⊚ | ⊚ | ⊚ |
| | Abrasion resistance | ○ | ○ | ○ | ○ | ○ |
| | Outer appearance | ○ | ⊚ | ○ | ○ | ⊚ |
| | Fingerprint stain removability | ⊚ | ⊚ | ⊚ | ⊚ | ⊚ |
| | Light resistance | Δ | Δ | Δ | ○ | ○ |
| | Lubricity | ⊚ | ⊚ | ○ | ⊚ | ⊚ |

TABLE 2

| | | | | Ex. | | |
|---|---|---|---|---|---|---|
| | | 22 | 23 | 24 | 25 | 26 |
| Fluorinated ether compound/composition | Type | Compound (1F-1) | Composition (7): compound (2A-1) + By-product | Composition (8): compound (4-1) + By-product | Composition (9): compound (5-1) + By-product | Composition (10): compound (5-2) + By-product |
| | Conversion (%) in hydrosilylation | 100 | 100 | 100 | 100 | 100 |
| | Selectivity (%) in hydrosilylation | 100 | 84 | 85 | 87 | 85 |
| Dry coating method | Initial contact angle Water | ⊚ | Δ | ⊚ | ⊚ | ○ |
| | n-Hexadecane | ⊚ | Δ | ⊚ | ⊚ | ⊚ |
| | Abrasion resistance | ○ | × | × | × | × |
| Wet coating method | Initial contact angle Water | ⊚ | Δ | ⊚ | ⊚ | ○ |
| | n-Hexadecane | ⊚ | Δ | ⊚ | ⊚ | ⊚ |
| | Abrasion resistance | ○ | × | × | × | × |
| | Outer appearance | ○ | × | ○ | ○ | ⊚ |
| | Fingerprint stain removability | ⊚ | × | ○ | ⊚ | ⊚ |
| | Light resistance | ⊚ | × | Δ | × | × |
| | Lubricity | ○ | Δ | × | ⊚ | ⊚ |

TABLE 3

| | | Ex. | | | | | |
|---|---|---|---|---|---|---|---|
| | | 27 | 28 | 29 | 30 | 31 | 32 |
| Fluorinated ether compound | Type | Compound (1I-1) | Compound (1I-2) | Compound (1H-1) | Compound (1H-2) | Compound (1K-1) | Compound (1G-1) |
| | Conversion (%) in hydrosilylation | 100 | 100 | 100 | 100 | 100 | 100 |
| | Selectivity (%) in hydrosilylation | 100 | 100 | 100 | 100 | 100 | 100 |
| Dry coating method | Initial contact angle   Water | ⊚ | ⊚ | ○ | ○ | ○ | ⊚ |
| | n-Hexadecane | ⊚ | ⊚ | ⊚ | ⊚ | ⊚ | ⊚ |
| | Abrasion resistance | ⊚ | ⊚ | ⊚ | ⊚ | ⊚ | ⊚ |
| Wet coating method | Initial contact angle   Water | ⊚ | ⊚ | ○ | ○ | ○ | ⊚ |
| | n-Hexadecane | ⊚ | ⊚ | ⊚ | ⊚ | ⊚ | ⊚ |
| | Abrasion resistance | ○ | ○ | ○ | ○ | ○ | ⊚ |
| | Outer appearance | ○ | ○ | ⊚ | ⊚ | ⊚ | ○ |
| | Fingerprint stain removability | ⊚ | ⊚ | ⊚ | ⊚ | ⊚ | ⊚ |
| | Light resistance | ○ | ○ | ○ | ○ | ○ | ⊚ |
| | Lubricity | ○ | ○ | ⊚ | ⊚ | ⊚ | ⊚ |

TABLE 4

| Ex. | | 51 | 52 | 53 |
|---|---|---|---|---|
| Fluorinated ether compound/ composition | Type | Compound (1D-2) | Compound (1E-2) | Compound (1F-2) |
| | Conversion (%) in hydrosilylation | 100 | 100 | 100 |
| | Selectivity (%) in hydrosilylation | 100 | 100 | 100 |
| Dry coating method | Initial contact angle   Water | ⊚ | ○ | ⊚ |
| | n-Hexadecane | ⊚ | ⊚ | ⊚ |
| | Abrasion resistance | ⊚ | ⊚ | ⊚ |
| Wet coating method | Initial contact angle   Water | ⊚ | ○ | ⊚ |
| | n-Hexadecane | ⊚ | ⊚ | ⊚ |
| | Abrasion resistance | ○ | ○ | ○ |
| | Outer appearance | ○ | ⊚ | ○ |

In Ex. 17 to 22, 27 to 32 and 51 to 53 wherein the present compound having three hydrolyzable silyl groups at one terminal, or a composition containing the present compound, was used, the water/oil repellency, abrasion resistance, outer appearance, fingerprint stain removability, light resistance and lubricity were excellent.

In Ex. 23 wherein a composition containing the compound (2A-1) having three hydrolyzable silyl groups at both terminals, the abrasion resistance, outer appearance, fingerprint stain removability and light resistance were inferior. The reason as to why the fingerprint stain removability was inferior, is considered to be such that unreacted terminal groups reduced the surface physical properties. The reason as to why the outer appearance and abrasion resistance were inferior, is considered to be due to reduction in uniformity due to agglomeration of the terminal non-fluorine portions. The reason for the inferior abrasion resistance is considered to be such that both terminals were fixed to the substrate.

In Ex. 24 wherein a composition containing the compound (4-1) wherein a poly(oxyperfluoroalkylene) chain had a branched structure, was used, the lubricity was significantly reduced by a decrease in molecular mobility due to the branched structure, and it is considered that abrasion resistance was also thereby greatly reduced.

In Ex. 25 and 26 wherein a composition containing the compound (5-1) or compound (5-2) having only one hydrolyzable silyl group at one terminal, was used, the abrasion resistance and light resistance were inferior.

Ex. 33 to 47: Production and Evaluation of Articles

Compound (3A-1) isolated in Ex. 1-1, was prepared.

The composition containing compound (1B-1) obtained in Ex. 2-3 was purified to obtain the compound (1B-1).

The composition containing compound (2A-1) obtained in Ex. 7-3 was purified to obtain the compound (2A-1).

In the proportions shown in Table 5, the compound (1B-1), the compound (2A-1) and the compound (3A-1) were mixed to prepare compositions. By using each composition, an article was prepared by the above-described wet coating method. With respect to the article, measurement of the contact angle and evaluation of the abrasion resistance and lubricity were carried out. The results are shown in Table 5.

TABLE 5

| | \multicolumn{15}{c}{Ex.} | | | | | | | | | | | | | | |
|---|---|---|---|---|---|---|---|---|---|---|---|---|---|---|---|
| | 33 | 34 | 35 | 36 | 37 | 38 | 39 | 40 | 41 | 42 | 43 | 44 | 45 | 46 | 47 |
| Compound (3A-1) (%) | 0 | 0 | 0 | 0 | 0 | 5 | 10 | 20 | 30 | 40 | 5 | 10 | 15 | 25 | 30 |
| Compound (1B-1) (%) | 95 | 90 | 80 | 70 | 60 | 95 | 90 | 80 | 70 | 60 | 90 | 80 | 70 | 50 | 40 |
| Compound (2A-1) (%) | 5 | 10 | 20 | 30 | 40 | 0 | 0 | 0 | 0 | 0 | 5 | 10 | 15 | 25 | 30 |
| Initial contact angle Water | ○ | ○ | ○ | ○ | ○ | ○ | ○ | ○ | ○ | ○ | ○ | ○ | ○ | ○ | Δ |
| n-Hexadecane | ◎ | ◎ | ◎ | ○ | ◎ | ◎ | ◎ | ◎ | ◎ | ◎ | ◎ | ◎ | ◎ | ○ | ○ |
| Abrasion resistance | ◎ | ◎ | ○ | Δ | X | ○ | ○ | ○ | Δ | X | ◎ | ◎ | ○ | X | X |
| Lubricity | ◎ | ◎ | ○ | Δ | X | ◎ | ◎ | ◎ | ◎ | ◎ | ◎ | ◎ | ◎ | ○ | Δ |

From Ex. 33 to 37, it was found that in a case where when the compound (2A-1) having three hydrolyzable silyl groups at both terminals, was added to the present compound having three hydrolyzable silyl groups at one terminal, when the proportion of the compound (2A-1) was less than 40 mass %, the surface layer had a practical performance. As the proportion of the compound (2A-1) was increased, the abrasion resistance and lubricity tended to decrease.

From Ex. 38 to 42, it was found that in a case where the compound (3A-1) having no hydrolyzable silyl group at both terminals, was added to the present compound having three hydrolyzable silyl groups at one terminal, when the proportion of the compound (3A-1) was less than 40 mass %, the surface layer had a practical performance. As the proportion of the compound (3A-1) was increased, the abrasion resistance tended to decrease.

From Ex. 43 to 47, it was found that in a case where the compound (2A-1) having three hydrolyzable silyl groups at both terminals and the compound (3A-1) having no hydrolyzable silyl group at both terminals were simultaneously added to the present compound having three hydrolyzable silyl groups at one terminal, when the total proportion of the compound (2A-1) and the compound (3A-1) was less than 40 mass %, the surface layer had a practical performance. As the total proportion of the compound (2A-1) and the compound (3A-1) was increased, the abrasion resistance tended to decrease.

INDUSTRIAL APPLICABILITY

The fluorinated ether compound of the present invention can be suitably used for surface treatment for imparting water/oil repellency to the surface of a substrate or the like constituting the surface to be touched with a finger, of a touch panel.

This application is a continuation of PCT Application No. PCT/JP2016/075354, filed on Aug. 30, 2016, which is based upon and claims the benefit of priority from Japanese Patent Application No. 2015-171986 filed on Sep. 1, 2015. The contents of those applications are incorporated herein by reference in their entireties.

What is claimed is:

1. A fluorinated ether compound represented by formula (1):

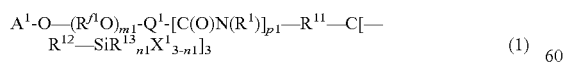  (1)

wherein
$A^1$ is a $C_{1-20}$ perfluoroalkyl group,
$R^{f1}$ is a fluoroalkylene group having no branched structure,
m1 is an integer of from 2 to 210,
$(R^{f1}O)_{m1}$ is optionally one composed of at least two types of $R^{f1}O$,
$Q^1$ is a single bond or a fluoroalkylene group having no branched structure,
$R^1$ is a hydrogen atom or an alkyl group,
p1 is 0 or 1,
$R^{11}$ is a single bond, an alkylene group, an alkylene group having an etheric oxygen atom at a terminal thereof, which is the terminal on the side bonded to $C[-R^{12}-SiR^{13}{}_{n1}X^1{}_{3-n1}]_3$, an alkylene group with at least two carbon atoms, having an etheric oxygen atom between two carbon atoms, or an alkylene group with at least two carbon atoms, having an etheric oxygen atom between two carbon atoms and at a terminal thereof which is the terminal on the side bonded to $C[-R^{12}-SiR^{13}{}_{n1}X^1{}_{3-n1}]_3$,
$R^{12}$ is an alkylene group,
$R^{13}$ is a hydrogen atom or a monovalent hydrocarbon group,
$X^1$ is a hydrolyzable group,
n1 is an integer of from 0 to 2, and
three $[-R^{12}-SiR^{13}{}_{n1}X^1{}_{3-n1}]$ are optionally not all the same group.

2. The fluorinated ether compound according to claim 1, wherein the fluorinated ether compound represented by the formula (1) is a fluorinated ether compound represented by formula (1-1):

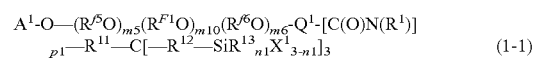  (1-1)

wherein $A^1$, $Q^1$, $R^1$, p1, $R^{11}$, $R^{12}$, $R^{13}$, $X^1$ and n1 are the same as in the formula (1),
$R^{F1}$ is a perfluoroalkylene group having no branched structure, m10 is an integer of at least 2, and $(R^{F1}O)_{m10}$ is optionally one composed of at least two types of $R^{F1}O$,
$R^{f5}$ is a fluoroalkylene group comprising at least one hydrogen atom and having no branched structure, m5 is an integer of from 0 to 4, and when m5 is an integer of from 2 to 4, $(R^{f5}O)_{m5}$ is optionally one composed of at least two types of $R^{f5}O$,
$R^{f6}$ is a fluoroalkylene group comprising at least one hydrogen atom and having no branched structure, m6 is an integer of from 0 to 4, and when m6 is an integer of from 2 to 4, $(R^{f6}O)_{m6}$ is optionally one composed of at least two types of $R^{f6}O$, and
m10+m5+m6=m1.

3. The fluorinated ether compound according to claim 2, wherein $R^{F1}$ is a $C_{1-6}$ perfluoroalkylene group, and $R^{f5}$ and $R^{f6}$ are each independently a $C_{2-6}$ fluoroalkylene group.

4. The fluorinated ether compound according to claim 2, wherein $R^{f5}$ and $R^{f6}$ are each independently a fluoroalkylene group having one or two hydrogen atoms.

5. The fluorinated ether compound according to claim 2, wherein when p1 is 0, m6 is 1 or 2 and $Q^1$ is a single bond, and $(R^{f6}O)$ bonded to $R^{11}$ is a group represented by $(R^{f7}CH_2O)$, wherein $R^{f7}$ is a perfluoroalkylene group or a fluoroalkylene group having a hydrogen atom, the number of carbon atoms of which is less by one than $R^{f6}$, and when p1 is 1, m6 is 0 and $Q^1$ is a fluoroalkylene group.

6. The fluorinated ether compound according to claim 2, wherein m10 is at least 5.

7. The fluorinated ether compound according to claim 1, wherein when $Q^1$ is a fluoroalkylene group, which is a $C_{1-6}$ perfluoroalkylene group.

8. The fluorinated ether compound according to claim 1, wherein when p1 is 0, $R^{11}$ is a $C_{1-4}$ alkylene group, and when p1 is 1, $R^{11}$ is a single bond or a $C_{1-4}$ alkylene group.

9. The fluorinated ether compound according to claim 1, wherein $R^{12}$ is a $C_{2-6}$ alkylene group.

10. The fluorinated ether compound according to claim 1, which has a number average molecular weight of from 500 to 20,000.

11. A fluorinated ether composition comprising the fluorinated ether compound as defined in claim 1, and an additional fluorinated ether compound other than the fluorinated ether compound represented by the formula (1), wherein the total proportion of the fluorinated ether compound represented by the formula (1) and the additional fluorinated ether compound in the fluorinated ether composition is from 80 to 100 mass %, and the proportion of the additional fluorinated ether compound to the total of the fluorinated ether compound represented by the formula (1) and the additional fluorinated ether compound is more than 0 mass % and less than 40 mass %.

12. The fluorinated ether composition according to claim 11, wherein the additional fluorinated ether compound is at least one member selected from the group consisting of a fluorinated ether compound (2), a fluorinated ether compound (3) and a fluorinated ether compound (4), wherein the fluorinated ether compound (2) is a fluorinated ether compound, in which a group having $-C[-R^{12}-SiR^{13}{}_{n1}X^1{}_{3-n1}]_3$ is bonded to both sides of $(R^{f1}O)_{m1}$, the fluorinated ether compound (3) is a fluorinated ether compound, in which a group having $A^1$ is bonded to both sides of $(R^{f1}O)_{m1}$, and the fluorinated ether compound (4) is a fluorinated ether compound, in which in the formula (1), $-C[-R^{12}-SiR^{13}{}_{n1}X^1{}_{3-n1}]_3$ is substituted by $-C[-R^{12}-SiR^{13}{}_{n1}X^1{}_{3-n1}]_{3-t}[-R^{15}]_t$, wherein $R^{15}$ is an unsaturated bond-containing group which becomes $-R^{12}-SiR^{13}{}_{n1}X^1{}_{3-n1}$ by addition of $HSiR^{13}{}_{n1}X^1{}_{3-n1}$, or an isomer group of the unsaturated bond-containing group, and t is an integer of 1 to 3.

13. A coating liquid comprising a fluorinated ether compound as defined in claim 1, and a liquid medium.

14. A coating liquid comprising a fluorinated ether composition as defined in claim 11, and a liquid medium.

15. An article comprising a surface layer which is formed of a fluorinated ether compound as defined in claim 1.

16. An article comprising a surface layer which is formed of a fluorinated ether composition as defined in claim 11.

* * * * *